United States Patent
Chin et al.

(10) Patent No.: US 7,972,265 B1
(45) Date of Patent: **\*Jul. 5, 2011**

(54) DEVICE AND METHOD FOR REMOTE VESSEL LIGATION

(75) Inventors: Albert K. Chin, Palo Alto, CA (US);
Edwin J. Hlavka, Palo Alto, CA (US);
John P. Lunsford, San Carlos, CA (US);
Jeffrey W. Baxter, San Jose, CA (US)

(73) Assignee: Maquet Cardiovascular, LLC, San Jose, CA (US)

( * ) Notice: Subject to any disclaimer, the term of this patent is extended or adjusted under 35 U.S.C. 154(b) by 854 days.

This patent is subject to a terminal disclaimer.

(21) Appl. No.: 10/897,157

(22) Filed: Jul. 21, 2004

Related U.S. Application Data

(63) Continuation of application No. 10/052,016, filed on Jan. 16, 2002, now Pat. No. 6,830,546, which is a continuation of application No. 09/521,279, filed on Mar. 7, 2000, now Pat. No. 6,348,037, which is a continuation of application No. 09/200,218, filed on Nov. 25, 1998, now Pat. No. 6,162,173, which is a continuation-in-part of application No. 09/102,723, filed on Jun. 22, 1998, now Pat. No. 5,895,353.

(51) Int. Cl.
*A61B 17/02* (2006.01)
(52) U.S. Cl. ........................ 600/206; 600/235
(58) Field of Classification Search .............. 600/206, 600/235, 212; 606/159, 190
See application file for complete search history.

(56) References Cited

U.S. PATENT DOCUMENTS

| | | | |
|---|---|---|---|
| 79,015 | A | 6/1868 | Schulz |
| 1,083,386 | A | 1/1914 | Chapman |
| 1,422,826 | A | 7/1922 | Brown |
| 1,683,708 | A | 9/1928 | Wappler |
| 1,727,495 | A | 9/1929 | Wappler |
| 1,731,069 | A | 10/1929 | Herman |
| 1,741,461 | A | 12/1929 | Herman |
| 1,798,902 | A | 3/1931 | Raney |
| 1,867,624 | A | 7/1932 | Hoffman |
| 1,881,250 | A | 10/1932 | Tomlinson |

(Continued)

FOREIGN PATENT DOCUMENTS

AU 199935034 (A1) 6/1999

(Continued)

OTHER PUBLICATIONS

Historical Development of VasoView by Albert Chin, Sep. 11, 2008.

(Continued)

*Primary Examiner* — Ralph A Lewis
(74) *Attorney, Agent, or Firm* — Vista IP Law Group, LLP

(57) ABSTRACT

A retractor and a surgical tool are positioned at the distal end of the cannula. A dissection cradle is located at the distal end of a distal portion of the retractor that is resiliently skewed relative to the cannula axis, and includes two substantially parallel, spaced legs with the retractor shaped in a loop therebetween. The procedure includes locating a vessel and side branch of interest and extending the retractor to retain the vessel in the dissection cradle to urge the vessel away from the axis of the cannula in order to isolate a side branch for exposure to the surgical tool.

28 Claims, 13 Drawing Sheets

U.S. PATENT DOCUMENTS

| | | | |
|---|---|---|---|
| 1,978,495 A | 10/1934 | Landau |
| 2,001,169 A | 5/1935 | Wallace |
| 2,002,594 A | 5/1935 | Wappler |
| 2,004,559 A | 6/1935 | Wappler et al. |
| 2,011,169 A | 8/1935 | Wappler |
| 2,012,937 A | 9/1935 | Beuoy |
| 2,028,635 A | 1/1936 | Wappler |
| 2,162,681 A | 6/1939 | Ryan |
| 2,220,720 A | 11/1940 | Jett |
| 2,227,727 A | 1/1941 | Leggiardo |
| 2,316,297 A | 4/1943 | Southerland |
| 2,821,190 A | 1/1958 | Chase |
| 2,840,070 A | 6/1958 | Tofflemire |
| 2,868,206 A | 1/1959 | Stoesser |
| 2,944,552 A | 7/1960 | Canon |
| 3,185,155 A | 5/1965 | Slaten |
| 3,224,320 A | 12/1965 | Knudsen |
| 3,297,022 A | 1/1967 | Wallace |
| 3,313,294 A | 4/1967 | Uddenberg |
| 3,336,916 A | 8/1967 | Edlich |
| 3,357,433 A | 12/1967 | Fourestier et al. |
| 3,568,677 A | 3/1971 | Nolan et al. |
| 3,613,682 A | 10/1971 | Naylor |
| 3,625,202 A | 12/1971 | Oyoshirhara |
| 3,805,793 A | 4/1974 | Wright |
| 3,835,841 A | 9/1974 | Terada |
| 3,856,016 A | 12/1974 | Davis |
| 3,857,386 A | 12/1974 | Ashbell |
| 3,866,601 A | 2/1975 | Russell |
| 3,882,854 A | 5/1975 | Hulka |
| 3,924,608 A | 12/1975 | Mitsui |
| 3,934,115 A | 1/1976 | Peterson |
| 3,980,861 A | 9/1976 | Fakunaga |
| RE29,088 E | 12/1976 | Shaw |
| 4,011,872 A | 3/1977 | Komiya |
| 4,031,898 A | 6/1977 | Hiltebrandt et al. |
| 4,038,987 A | 8/1977 | Komiya |
| 4,052,980 A | 10/1977 | Grams et al. |
| 4,132,227 A | 1/1979 | The |
| 4,175,545 A | 11/1979 | Termanini |
| 4,178,920 A | 12/1979 | Cawood et al. |
| 4,190,042 A | 2/1980 | Sinnreich |
| 4,196,734 A | 4/1980 | Harris |
| 4,232,660 A | 11/1980 | Coles |
| 4,257,420 A | 3/1981 | Terayama |
| 4,359,052 A | 11/1982 | Staub |
| 4,362,160 A | 12/1982 | Hiltebrandt |
| 4,369,768 A | 1/1983 | Vukovic |
| 4,372,295 A | 2/1983 | Heckele |
| 4,418,692 A | 12/1983 | Guay |
| 4,423,727 A | 1/1984 | Widran et al. |
| 4,428,746 A | 1/1984 | Mendez |
| 4,440,170 A | 4/1984 | Golden et al. |
| 4,493,321 A | 1/1985 | Leather |
| 4,493,711 A | 1/1985 | Chin et al. |
| 4,499,898 A | 2/1985 | Knepshield |
| 4,499,899 A | 2/1985 | Lyons, III |
| 4,516,574 A | 5/1985 | Hewes, Jr. |
| 4,516,575 A | 5/1985 | Gerhard et al. |
| 4,556,058 A | 12/1985 | Green |
| 4,557,255 A | 12/1985 | Goodman |
| 4,562,832 A | 1/1986 | Wilder et al. |
| 4,586,919 A | 5/1986 | Taheri |
| 4,587,968 A | 5/1986 | Price |
| 4,597,030 A | 6/1986 | Brody et al. |
| 4,597,389 A | 7/1986 | Ibrahim et al. |
| 4,600,940 A | 7/1986 | Sluyter |
| 4,607,622 A | 8/1986 | Fritch |
| 4,638,802 A | 1/1987 | Okada |
| 4,646,738 A | 3/1987 | Trott |
| 4,649,917 A | 3/1987 | Karasawa |
| 4,651,733 A | 3/1987 | Mobin-Uddin |
| 4,653,476 A | 3/1987 | Bonnet |
| 4,654,024 A | 3/1987 | Crittenden |
| 4,656,999 A | 4/1987 | Storz |
| 4,657,018 A | 4/1987 | Hakky |
| 4,662,068 A | 5/1987 | Polonsky |
| 4,667,655 A | 5/1987 | Ogiu et al. |
| 4,700,694 A | 10/1987 | Shishido |
| 4,702,246 A | 10/1987 | Ellis et al. |
| 4,726,370 A | 2/1988 | Karasawa et al. |
| 4,744,363 A | 5/1988 | Hasson |
| 4,745,908 A | 5/1988 | Wardle |
| 4,754,754 A | 7/1988 | Garito et al. |
| 4,759,348 A | 7/1988 | Cawood |
| 4,759,364 A | 7/1988 | Boebel |
| 4,762,120 A | 8/1988 | Hussein |
| 4,768,508 A | 9/1988 | Chin et al. |
| 4,772,093 A | 9/1988 | Abele et al. |
| 4,773,394 A | 9/1988 | Reichstein et al. |
| 4,779,611 A | 10/1988 | Grooters et al. |
| 4,793,346 A | 12/1988 | Mindich |
| 4,819,620 A | 4/1989 | Okutsu |
| 4,819,633 A | 4/1989 | Bauer et al. |
| 4,821,718 A | 4/1989 | Uldall |
| 4,838,246 A | 6/1989 | Hahn et al. |
| 4,858,595 A | 8/1989 | Buess et al. |
| 4,862,874 A | 9/1989 | Kellner |
| 4,865,019 A | 9/1989 | Phillips |
| 4,867,138 A | 9/1989 | Kubota et al. |
| 4,869,268 A | 9/1989 | Yoon |
| 4,874,375 A | 10/1989 | Ellison |
| 4,877,016 A | 10/1989 | Kantor et al. |
| 4,909,789 A | 3/1990 | Taguchi et al. |
| 4,919,129 A | 4/1990 | Weber, Jr. et al. |
| 4,924,851 A | 5/1990 | Ognier et al. |
| 4,924,882 A | 5/1990 | Donovan |
| 4,932,952 A | 6/1990 | Wojciechowicz, Jr. |
| 4,936,842 A | 6/1990 | D'Amelio et al. |
| 4,950,278 A | 8/1990 | Sachse et al. |
| 4,959,067 A | 9/1990 | Muller |
| 4,966,596 A | 10/1990 | Kuntz et al. |
| 4,985,030 A | 1/1991 | Melzer et al. |
| 4,991,565 A | 2/1991 | Takahash et al. |
| 4,994,062 A | 2/1991 | Nishigaki et al. |
| 4,997,419 A | 3/1991 | Lakatos et al. |
| 4,997,436 A | 3/1991 | Oberlander |
| 4,998,527 A | 3/1991 | Meyer |
| 4,998,972 A | 3/1991 | Chin et al. |
| 5,007,907 A | 4/1991 | Nishigaki et al. |
| 5,007,908 A | 4/1991 | Rydell |
| 5,011,490 A | 4/1991 | Fischell et al. |
| 5,013,312 A | 5/1991 | Parins et al. |
| 5,020,514 A | 6/1991 | Heckele |
| 5,025,778 A | 6/1991 | Silverstein et al. |
| 5,026,370 A | 6/1991 | Lottick |
| 5,026,383 A | 6/1991 | Nobles |
| 5,035,232 A | 7/1991 | Lutze et al. |
| 5,037,433 A | 8/1991 | Wilk et al. |
| 5,047,038 A | 9/1991 | Peters et al. |
| 5,049,154 A | 9/1991 | Quadri |
| 5,053,041 A | 10/1991 | Ansari et al. |
| 5,100,420 A | 3/1992 | Green et al. |
| 5,171,311 A | 12/1992 | Rydell et al. |
| 5,181,919 A | 1/1993 | Bergman et al. |
| 5,188,630 A | 2/1993 | Christoudias |
| 5,190,541 A | 3/1993 | Abele et al. |
| 5,197,971 A | 3/1993 | Bonutti |
| 5,201,752 A | 4/1993 | Brown et al. |
| 5,213,093 A | 5/1993 | Swindle |
| 5,217,001 A | 6/1993 | Nakao et al. |
| 5,217,441 A | 6/1993 | Shichman |
| 5,230,621 A | 7/1993 | Jacoby |
| 5,251,613 A | 10/1993 | Adair |
| 5,258,006 A | 11/1993 | Rydell et al. |
| 5,259,366 A | 11/1993 | Reydel et al. |
| 5,269,753 A | 12/1993 | Wilk |
| 5,269,785 A | 12/1993 | Bonutti |
| 5,271,380 A | 12/1993 | Riek et al. |
| 5,271,385 A | 12/1993 | Bailey |
| 5,273,026 A | 12/1993 | Wilk |
| 5,275,608 A | 1/1994 | Forman et al. |
| 5,279,546 A | 1/1994 | Mische et al. |
| 5,284,128 A | 2/1994 | Hart |
| 5,284,478 A | 2/1994 | Nobles et al. |
| 5,290,284 A | 3/1994 | Adair |
| 5,300,036 A | 4/1994 | Mueller et al. |

| | | | | | | |
|---|---|---|---|---|---|---|
| 5,312,423 A | 5/1994 | Rosenbluth et al. | | 5,575,756 A | 11/1996 | Karasawa et al. |
| 5,318,564 A | 6/1994 | Eggers | | 5,588,581 A | 12/1996 | Conlon et al. |
| 5,318,586 A | 6/1994 | Ereren | | 5,591,183 A | 1/1997 | Chin |
| 5,320,115 A | 6/1994 | Kenna | | 5,599,349 A | 2/1997 | D'Amelio |
| 5,322,503 A | 6/1994 | Desai | | 5,601,580 A | 2/1997 | Goldberg et al. |
| 5,334,150 A | 8/1994 | Kaali | | 5,601,581 A | 2/1997 | Fogarty et al. |
| 5,336,231 A | 8/1994 | Adair | | 5,618,307 A | 4/1997 | Donlon et al. |
| 5,337,736 A | 8/1994 | Reddy | | 5,626,587 A | 5/1997 | Bishop et al. |
| 5,337,738 A | 8/1994 | Reddy | | 5,630,787 A | 5/1997 | Yabe et al. |
| 5,339,803 A | 8/1994 | Mayzels et al. | | 5,630,795 A | 5/1997 | Kuramoto et al. |
| 5,345,927 A | 9/1994 | Bonutti | | 5,634,584 A | 6/1997 | Okorocha et al. |
| 5,346,504 A | 9/1994 | Ortiz et al. | | 5,634,924 A | 6/1997 | Turkel et al. |
| 5,352,219 A | 10/1994 | Reddy | | 5,653,722 A | 8/1997 | Kieturakis |
| 5,354,291 A | 10/1994 | Bales et al. | | 5,656,012 A | 8/1997 | Sienkiewicz |
| 5,359,995 A | 11/1994 | Sewell, Jr. | | 5,658,282 A | 8/1997 | Daw et al. |
| 5,366,476 A | 11/1994 | Noda | | 5,662,585 A | 9/1997 | Willis et al. |
| 5,368,015 A | 11/1994 | Wilk | | 5,662,588 A | 9/1997 | Iida |
| 5,370,109 A | 12/1994 | Cuny | | 5,662,662 A | 9/1997 | Bishop et al. |
| 5,373,840 A | 12/1994 | Knighton | | 5,665,096 A | 9/1997 | Yoon |
| 5,374,277 A | 12/1994 | Hassler | | 5,667,480 A | 9/1997 | Knight et al. |
| 5,376,076 A | 12/1994 | Kaali | | 5,669,906 A | 9/1997 | Grossi et al. |
| 5,380,291 A | 1/1995 | Kaali | | 5,673,840 A | 10/1997 | Schulze et al. |
| 5,383,889 A | 1/1995 | Warner et al. | | 5,680,982 A | 10/1997 | Schulze et al. |
| 5,385,572 A | 1/1995 | Nobles et al. | | 5,683,349 A | 11/1997 | Makower et al. |
| 5,386,818 A | 2/1995 | Scheebaum et al. | | 5,685,820 A | 11/1997 | Riek et al. |
| 5,391,178 A | 2/1995 | Yapor | | 5,688,269 A | 11/1997 | Newton et al. |
| 5,395,367 A | 3/1995 | Wilk | | 5,690,606 A | 11/1997 | Slotman |
| 5,395,383 A | 3/1995 | Adams et al. | | 5,695,448 A | 12/1997 | Kimura et al. |
| 5,397,335 A | 3/1995 | Gresal et al. | | 5,700,236 A | 12/1997 | Sauer et al. |
| 5,403,312 A | 4/1995 | Yates et al. | | 5,702,408 A | 12/1997 | Wales et al. |
| 5,411,466 A | 5/1995 | Hess | | 5,702,412 A | 12/1997 | Popov et al. |
| 5,411,483 A | 5/1995 | Loomas et al. | | 5,704,372 A | 1/1998 | Moll |
| 5,417,697 A | 5/1995 | Wilk et al. | | 5,704,534 A | 1/1998 | Huitema et al. |
| 5,419,309 A | 5/1995 | Biehl | | 5,707,389 A | 1/1998 | Louw et al. |
| 5,423,813 A | 6/1995 | Kaiser et al. | | 5,713,505 A | 2/1998 | Huitema |
| 5,424,877 A | 6/1995 | Tsuyuki et al. | | 5,716,352 A | 2/1998 | Viola et al. |
| 5,425,355 A | 6/1995 | Kulick | | 5,718,714 A | 2/1998 | Livneh |
| 5,425,357 A | 6/1995 | Moll et al. | | 5,720,761 A | 2/1998 | Kaali |
| 5,431,151 A | 7/1995 | Riek et al. | | 5,722,934 A * | 3/1998 | Knight et al. .................. 600/201 |
| 5,441,041 A | 8/1995 | Sauer et al. | | 5,725,479 A | 3/1998 | Knight et al. |
| 5,441,498 A | 8/1995 | Perkins | | 5,728,119 A | 3/1998 | Smith |
| 5,447,513 A | 9/1995 | Davison et al. | | 5,730,748 A | 3/1998 | Fogarty et al. |
| 5,448,990 A | 9/1995 | De Faria-Correa | | 5,738,628 A | 4/1998 | Sierocuk et al. |
| 5,450,842 A * | 9/1995 | Tovey et al. .................... 600/206 | | 5,743,880 A | 4/1998 | Hlavka |
| 5,452,732 A | 9/1995 | Bircoll | | 5,749,870 A | 5/1998 | Gloth et al. |
| 5,460,629 A | 10/1995 | Shlain et al. | | 5,752,966 A | 5/1998 | Chang |
| 5,468,248 A | 11/1995 | Chin et al. | | 5,759,150 A | 6/1998 | Konou et al. |
| 5,474,057 A | 12/1995 | Makower et al. | | 5,759,183 A | 6/1998 | VanDusseldorp |
| 5,486,155 A | 1/1996 | Muller et al. | | 5,759,188 A | 6/1998 | Yoon |
| 5,489,290 A | 2/1996 | Furnish | | 5,762,606 A | 6/1998 | Minnich |
| 5,490,836 A | 2/1996 | Desai | | 5,766,169 A | 6/1998 | Fritzsch et al. |
| 5,496,317 A | 3/1996 | Goble et al. | | 5,766,215 A | 6/1998 | Muri et al. |
| 5,496,345 A | 3/1996 | Kieturakis et al. | | 5,772,576 A | 6/1998 | Knighton et al. |
| 5,501,654 A | 3/1996 | Failla et al. | | 5,779,728 A | 7/1998 | Lunsford |
| 5,505,686 A | 4/1996 | Willis et al. | | 5,795,331 A | 8/1998 | Cragg et al. |
| 5,507,755 A | 4/1996 | Gresal et al. | | 5,817,013 A | 10/1998 | Ginn et al. |
| 5,509,922 A | 4/1996 | Aranyi et al. | | 5,843,121 A | 12/1998 | Yoon |
| 5,511,564 A | 4/1996 | Wilk | | RE36,043 E | 1/1999 | Knighton |
| 5,512,037 A | 4/1996 | Russell et al. | | 5,857,961 A | 1/1999 | Vanden Hoek et al. |
| 5,514,151 A | 5/1996 | Fogarty et al. | | 5,871,496 A * | 2/1999 | Ginn et al. .................... 606/190 |
| 5,514,153 A | 5/1996 | Bonutti | | 5,895,352 A | 4/1999 | Kleiner |
| 5,518,502 A | 5/1996 | Kaplan et al. | | 5,895,353 A * | 4/1999 | Lunsford et al. .............. 600/209 |
| 5,522,830 A | 6/1996 | Aranyi | | 5,897,487 A | 4/1999 | Ouchi |
| 5,533,496 A | 7/1996 | De Faria-Correa et al. | | 5,908,429 A | 6/1999 | Yoon |
| 5,535,759 A | 7/1996 | Wilk | | 5,913,870 A * | 6/1999 | DeFonzo et al. .............. 606/190 |
| 5,536,251 A | 7/1996 | Evard et al. | | 5,916,213 A | 6/1999 | Haissaguerre et al. |
| 5,549,605 A | 8/1996 | Hahnen | | 5,921,993 A | 7/1999 | Yoon |
| 5,549,636 A | 8/1996 | Li | | 5,925,058 A | 7/1999 | Smith |
| 5,549,637 A | 8/1996 | Crainich | | 5,928,135 A | 7/1999 | Knight et al. |
| 5,551,947 A | 9/1996 | Kaali | | 5,928,138 A | 7/1999 | Knight et al. |
| 5,554,101 A | 9/1996 | Matula et al. | | 5,938,620 A | 8/1999 | Hecke'e et al. |
| 5,558,620 A | 9/1996 | Heckele et al. | | 5,938,680 A * | 8/1999 | Ginn ........................ 606/190 |
| 5,564,615 A | 10/1996 | Bishop et al. | | 5,957,923 A | 9/1999 | Hahnen et al. |
| 5,569,164 A | 10/1996 | Lurz | | 5,957,936 A | 9/1999 | Yoon et al. |
| 5,569,183 A | 10/1996 | Kieturakis | | 5,984,937 A | 11/1999 | Morse et al. |
| 5,569,244 A | 10/1996 | Hahnen | | 5,984,938 A | 11/1999 | Yoon |
| 5,569,274 A | 10/1996 | Rapacki et al. | | 5,984,939 A | 11/1999 | Yoon |
| 5,569,291 A | 10/1996 | Privitera et al. | | 5,993,384 A * | 11/1999 | Lunsford et al. .............. 600/209 |
| 5,571,100 A | 11/1996 | Goble et al. | | 6,022,213 A * | 2/2000 | Harthun ........................ 431/158 |

| | | |
|---|---|---|
| 6,036,713 A | 3/2000 | Kieturakis |
| 6,059,802 A | 5/2000 | Ginn |
| 6,071,232 A | 6/2000 | Knighton |
| 6,080,102 A | 6/2000 | Konou et al. |
| 6,120,434 A | 9/2000 | Kimura et al. |
| 6,123,689 A | 9/2000 | To |
| 6,129,661 A | 10/2000 | Iafrati et al. |
| 6,162,173 A | 12/2000 | Chin et al. |
| 6,176,825 B1 | 1/2001 | Chin et al. |
| 6,186,825 B1 | 2/2001 | Rogiel et al. |
| 6,234,958 B1 | 5/2001 | Snoke et al. |
| 6,277,137 B1 | 8/2001 | Chin |
| 6,312,442 B1 | 11/2001 | Kieturakis et al. |
| 6,348,037 B1 * | 2/2002 | Chin et al. .................. 600/235 |
| 6,361,543 B1 | 3/2002 | Chin et al. |
| 6,387,043 B1 | 5/2002 | Yoon |
| 6,406,425 B1 * | 6/2002 | Chin et al. .................. 600/205 |
| 6,520,975 B2 | 2/2003 | Branco |
| 6,558,313 B1 | 5/2003 | Knighton et al. |
| 6,562,051 B1 | 5/2003 | Bolduc |
| 6,648,898 B1 | 11/2003 | Baxter |
| 6,660,016 B2 | 12/2003 | Lindsay |
| 6,673,087 B1 | 1/2004 | Chang |
| 6,702,813 B1 | 3/2004 | Baxter et al. |
| 6,705,986 B2 | 3/2004 | Fiegel et al. |
| 6,730,020 B2 | 5/2004 | Peng et al. |
| 6,749,609 B1 | 6/2004 | Lunsford |
| 6,752,756 B2 | 6/2004 | Lunsford et al. |
| 6,762,368 B2 | 7/2004 | Saputro |
| 6,811,546 B1 | 11/2004 | Callas |
| 6,814,696 B1 | 11/2004 | Chang et al. |
| 6,814,743 B2 | 11/2004 | Chin |
| 6,830,546 B1 | 12/2004 | Chin et al. |
| 6,884,248 B2 | 4/2005 | Bolduc |
| 6,899,670 B2 | 5/2005 | Peng |
| 6,963,792 B1 | 11/2005 | Green |
| 6,972,028 B2 | 12/2005 | Chin |
| 6,976,957 B1 | 12/2005 | Chin et al. |
| 7,033,357 B2 | 4/2006 | Baxter et al. |
| 7,066,875 B2 | 6/2006 | Knighton et al. |
| 7,097,665 B2 | 8/2006 | Stack |
| 7,146,984 B2 | 12/2006 | Stack |
| 7,211,040 B2 | 5/2007 | Knighton et al. |
| 7,214,180 B2 | 5/2007 | Chin |
| 7,226,409 B2 | 6/2007 | Peng |
| 7,264,587 B2 | 9/2007 | Chin |
| 7,288,096 B2 | 10/2007 | Chin |
| 7,326,178 B1 | 2/2008 | Lunsford et al. |
| 7,344,536 B1 | 3/2008 | Lunsford |
| 7,364,657 B2 | 4/2008 | Mandrusov |
| 7,384,423 B1 | 6/2008 | Chin |
| 7,398,781 B1 | 7/2008 | Chin |
| 7,431,725 B2 | 10/2008 | Stack |
| 7,476,198 B1 | 1/2009 | Chin et al. |
| 7,479,104 B2 | 1/2009 | Lau |
| 7,485,092 B1 | 2/2009 | Stewart |
| 2002/0183593 A1 | 12/2002 | Chin et al. |
| 2003/0187460 A1 | 10/2003 | Chin |
| 2003/0187461 A1 | 10/2003 | Chin |
| 2003/0236544 A1 | 12/2003 | Lunsford |
| 2004/0097792 A1 | 5/2004 | Moll |
| 2004/0102804 A1 | 5/2004 | Chin |
| 2004/0153098 A1 | 8/2004 | Chin |
| 2004/0153101 A1 | 8/2004 | Bolduc |
| 2004/0181242 A1 | 9/2004 | Stack |
| 2004/0216748 A1 | 11/2004 | Chin |
| 2004/0236231 A1 | 11/2004 | Knighton |
| 2004/0236310 A1 | 11/2004 | Chin |
| 2005/0192613 A1 | 9/2005 | Lindsay |
| 2005/0247320 A1 | 11/2005 | Stack |
| 2005/0261712 A1 | 11/2005 | Balbierz |
| 2005/0266109 A1 | 12/2005 | Chin |
| 2005/0267499 A1 | 12/2005 | Stack |
| 2006/0052660 A1 | 3/2006 | Chin |
| 2006/0079915 A1 | 4/2006 | Chin |
| 2006/0116746 A1 | 6/2006 | Chin |
| 2006/0206121 A1 | 9/2006 | Chin |
| 2006/0270900 A1 | 11/2006 | Chin |
| 2006/0271032 A1 | 11/2006 | Chin |
| 2006/0287574 A1 | 12/2006 | Chin |
| 2006/0287734 A1 | 12/2006 | Stack |
| 2007/0060932 A1 | 3/2007 | Stack |
| 2007/0118206 A1 | 5/2007 | Colgan |
| 2007/0162067 A1 | 7/2007 | Lunsford |
| 2007/0198043 A1 | 8/2007 | Cox |
| 2007/0219571 A1 | 9/2007 | Balbierz |
| 2007/0238917 A1 | 10/2007 | Peng |
| 2007/0276432 A1 | 11/2007 | Stack |
| 2008/0039879 A1 | 2/2008 | Chin |
| 2008/0065122 A1 | 3/2008 | Stack |
| 2008/0097523 A1 | 4/2008 | Bolduc |
| 2008/0103365 A1 | 5/2008 | Chin |
| 2008/0132892 A1 | 6/2008 | Lunsford |
| 2008/0145345 A1 | 6/2008 | Mandrusov |
| 2008/0145469 A1 | 6/2008 | Chin |
| 2008/0306333 A1 | 12/2008 | Chin |
| 2008/0306335 A1 | 12/2008 | Lau |
| 2009/0024156 A1 | 1/2009 | Chin |

FOREIGN PATENT DOCUMENTS

| | | |
|---|---|---|
| AU | 1999-42354 | 7/1999 |
| AU | 199942354 (A1) | 7/1999 |
| AU | 1999-035034 | 1/2000 |
| AU | 719712 | 8/2000 |
| AU | 2007-203086 | 7/2007 |
| CA | 2 244 164 | 1/1997 |
| CA | 2 274 270 | 12/1999 |
| CA | 2 279 661 | 2/2000 |
| CA | 2 592 766 | 6/2007 |
| DE | 24 15 263 (A1) | 10/1975 |
| DE | 3525917 (A1) | 2/1986 |
| DE | 3942589 (A1) | 7/1991 |
| EP | 0 131 347 | 1/1985 |
| EP | 0 243 714 (A2) | 11/1987 |
| EP | 0 341 943 | 11/1989 |
| EP | 0 664 104 | 7/1995 |
| EP | 0 681 811 A2 | 11/1995 |
| EP | 0 409 569 | 1/1997 |
| EP | 0 761 171 | 3/1997 |
| EP | 0 761 171 A2 | 3/1997 |
| EP | 0 761 171 B1 | 3/1997 |
| EP | 0 781 171 A2 | 3/1997 |
| EP | 00769270 | 4/1997 |
| EP | 0 867 148 | 9/1998 |
| EP | 0 980 673 | 2/2000 |
| EP | 0 980 673 (A2) | 2/2000 |
| FR | 2 265 344 | 10/1975 |
| GB | 2 082 459 | 3/1982 |
| GB | 2 195 540 | 4/1988 |
| JP | 7-27043 | 1/1995 |
| JP | 2802244 | 7/1998 |
| JP | 11-172954 | 6/1999 |
| JP | 11-225282 | 8/1999 |
| JP | 2000-037389 | 2/2000 |
| JP | 2007-509702 | 4/2007 |
| JP | 2007-175478 | 7/2007 |
| SU | 112367 | 6/1958 |
| SU | 510235 | 4/1976 |
| SU | 1371689 A1 | 2/1988 |
| WO | WO 91/08710 | 6/1991 |
| WO | WO 92/20291 | 11/1992 |
| WO | WO 94/18881 | 9/1994 |
| WO | WO 95/10982 | 4/1995 |
| WO | WO 95/19737 | 7/1995 |
| WO | WO 96/01130 | 1/1996 |
| WO | WO 96/30072 | 10/1996 |
| WO | WO 96/36287 | 11/1996 |
| WO | WO 97/16125 | 5/1997 |
| WO | WO 97/26831 | 7/1997 |
| WO | WO 97/33522 | 9/1997 |
| WO | WO 97/37701 | 10/1997 |
| WO | WO 98/02084 | 1/1998 |
| WO | WO 98/02102 | 1/1998 |
| WO | WO 98/06451 | 2/1998 |
| WO | WO 00/40139 | 7/2000 |
| WO | WO 00/40160 | 7/2000 |
| WO | WO 03/057062 A2 | 7/2003 |
| WO | WO 03/094758 A1 | 11/2003 |

| WO | WO 03/105706 | 12/2003 |
| --- | --- | --- |
| WO | WO 2004/066828 A2 | 8/2004 |
| WO | WO 2004/066829 A2 | 8/2004 |
| WO | WO 2004/073506 | 9/2004 |
| WO | WO 2005/006955 A2 | 1/2005 |
| WO | WO 2005/044079 A2 | 5/2005 |

OTHER PUBLICATIONS

Pending U.S. Appl. No. 10/897,157, filed Jul. 21, 2004.
Handwritten Notes, Oct. 17, 1996.
Clinical Results, May 13, 1992.
Page from Tachi Callas Lab Notebook, Jul. 1, 1997.
Chin Memo regarding Saphenous Vein Harvesting, May 17, 1995.
U.S. Appl. No. 60/148,130, filed Aug. 10, 1999, Chin.
U.S. Appl. No. 60/150,737, filed Aug. 25, 1999, Chin.
U.S. Appl. No. 08/269,666, filed Jul. 1, 1994, Chin.
U.S. Appl. No. 08/502,494, filed Mar. 14, 2000, Chin et al.
U.S. Appl. No. 08/593,533, filed Jan. 24, 1996, Chin.
U.S. Appl. No. 09/133,136, filed Aug. 12, 1998, Chin.
U.S. Appl. No. 09/227,393, filed Jan. 8, 1999, Lunsford et al.
U.S. Appl. No. 09/413,012, filed Oct. 5, 1999, Chin et al.
U.S. Appl. No. 09/635,721, filed Aug. 9, 2000, Chin.
U.S. Appl. No. 09/738,608, filed Dec. 14, 2000, Chin.
U.S. Appl. No. 09/739,595, filed Dec. 15, 2000, Chang.
U.S. Appl. No. 09/750,848, filed Dec. 27, 2000, Chin.
U.S. Appl. No. 10/345,666, filed Jan. 16, 2003, Stack.
U.S. Appl. No. 10/371,537, filed Feb. 21, 2003, Beavers.
U.S. Appl. No. 11/962,517, filed Dec. 21, 2007, Chin.
U.S. Appl. No. 90/004,301, filed Jul. 12, 1996, Knighton et al.
Mackenzie, The Use of Laryngoscope in Diseases of the Throat: with an essay on Hoarseness Loss of Voice, and Stridulous Breathing, In Relation to Nervo-Muscular Affection of the Larynx (1869).
Schwyzer, "On Bronchoscopy. With Report of a Case in Which a Foreign Body was Removed from the Right Lower Lobe of a Lung Through a Bronchoscope", Read before the Minnesota Academy of Medicine pp. 194-206 (Dec. 2, 1903).
Mathews, A Treatise on Diseases of the Rectum, Anus, and Signoid Flexure (1903).
Mayo, "The Surgical Treatment of Varicose Veins", The St. Paul Medical Journal, vol. VI, pp. 695-699 (1904).
Fenwick, "A Handbook of Clinical Electric-Light Cystoscopy" (1905).
Carrel et al.., "Uniterminal and Biterminal Venous Transplantations", Surgery, Gynecology and Obstetrics, vol. II, pp. 266-286 (1906).
Mayo, "Treatment of Varicose Veins", Surgery, Gynecology and Obstetrics, pp. 385-388 (1906).
Carrel et al., "Results of the Biterminal Transplantation of Veins", pp. 415-422 (1906).
Jackson, "Endothelioma of the Right Bronchus Removed by Peroral Bronchoscopy", The American Journal of the Medical Sciences. vol. CLIII. pp. 37-375 (1917).
Stern, "Resection of Obstruction at the Vesical Orifice; New Instruments Resectotherm; Resectoscope and New Method", Journal of American Medical Associtation, vol. 87, No. 21, pp. 1726-1730 (1926).
Chandler, "Internal Pneumolysis: Results of 110 Consecutive Operations", The Lancet, pp. 879-882 (Oct. 19, 1935).
Hurley, "Some Practical Guiding Principles for Closed Pneumonolysis", Canad. M.A.J., vol. 56, pp. 625-627 (Jun. 1947).
Bayliss, "Closed Intrapleural Pneumonolysis", Chest, vol. XIII, pp. 479-515 (1947).
Sarot et al., "Closed Pneumonolysis (Enucleation Technique)", Chest, vol. XVI, No. 5, pp. 509-542 (Nov. 1949).
Morris et al., "Arterial Bypass Below the Knee", Surgery, Gynecology & Obstetrics, vol. 108, pp. 321-332 (Jan.-Jun. 1959).
Hall, "The Great Saphenous Vein Used in Situ as an Arterial Shunt After Extirpation of the Vein Valves", Surgery, vol. 51. No. 4. pp. 492-495 (Apr. 1962).
Linton et al., "Autogenous Saphenous Vein Bypass Grafts in Femoropopliteal Obliterative Arterial Disease", Surgery, vol. 51. No. 1. pp. 62-73 (Jan.-Jun. 1962).

Palva, "Mediastinoscopy—A New Field for Bronchologists", Acta Oto-Laryngologica, vol. 53, Issue 2 & 3 (1961), http://www.informaworld.com/smpp/content.
Lore, "Tender Grip Forceps", The American Journal of Surgery, vol. 104, pp. 84-85 (Jul. 1962).
May et al., "Arterialized in Situ Saphenous Vein", Archives of Surgery, vol. 91, No. 5, pp. 743-750 (Nov. 1965).
Steptoe, "Abdominal Laparoscopy", Laparoscopy in Gynaecology, pp. 13-25 (1967).
Favaloro, "Saphenous Vein Graft in the Surgical Treatment of Coronary Artery Disease", The Journal of Thoracic and Cardiovascular Surgery, vol. 58. No. 2. (Aug. 1969).
Barner et al., "Late Failure of Arterialized in Situ Saphenous Vein", Archives of Surgery, vol. 99, pp. 781-786 (Dec. 1969).
Effler et al., "The Simple Approach to Direct Coronary Artery Surgery", The Journal of Thoracic and Cardiovascular Surgery, vol. 62, No. 4, pp. 503-510 (Oct. 1971).
Nagovitsyn, "Varicocide Treatment of Varicose Veins of the Lower Extremities" (1971).
Koontz et al., "Factors Influencing Patency of the Autogenous Vein-Femoropoliteal Bypass Grafts: An Analysis of 74 Cases". Surgery. vol. 71. No. 5. pp. 753-759 (May 1972).
Rizk et al., "Vascular Endoscopy", Radiology, vol. 106, No. 1, pp. 33-35 (Jan. 1973).
Balasegaram, "Hepatic Surgery: A Review of a Personal Series of 95 Major Resections", The Australian and New Zealand Journal of Surgery, vol. 42. No. 1, pp. 1-10 (Aug. 1972).
Brody et al., "Changes in Vein Grafts Following Aorto-Coronary Bypass Induced by Pressure and Ischemia", The Journal of Thoracic and Cardiovascular Surgery. vol. 64. No. 6. pp. 847-854 (Dec. 1972).
Jones et al., "Lesions Observed in Arterial Autogenous Vein Grafts", Cardiovascular Surgery, pp. 198-210 (1972).
Kern et al., "The Intimal Proliferation in Aortic-Coronary Saphenous Vein Grafts: Light and electron microscopic studies", American Heart Journal, pp. 771-777 (Dec. 1972).
Crispin et al., "Intravascular Observation and Surgery Using the Flexible Fibrescope", The Lancet, pp. 750-751 (Apr. 7, 1973).
Abbott et al., "Structural Changes During Preparation of Autogenous Venous Grafts", Surgery, vol. 76, No. 6, pp. 1031-1040 (Dec. 1974).
Brook, "A historical review of the histology of patent autogenous vein grafts and vein patches", The Journal of Cardiovascular Surgery. vol. 16. No. 1. pp. 43-52 (Jan.-Feb. 1975).
Shepherd et al., "Physical Characteristics of Venous System in Man", Veins and their Control, pp. 171-172 (1975).
Gittes, "Operative Nephroscopy", J Urol. (Aug. 1976), http://www.ncbi.nlm.nih.gov/sites/entrez.
Cutler et al., "Autologous Saphenous vein femoropopliteal bypass: Analysis of 298 cases", Surgery, vol. 79, No. 3, pp. 325-331 (Mar. 1976).
Lukomsky et al., "Diagnosing Phasic Nature of Pulmonary Carcinoma by Means of Combined Mediastino-Laparoscopy" 1976.
Corson, "Chapter 10: Operating Room Preparation and Basic Techniques", Laparoscopy, pp. 88-102 (1977).
Gottlob, "The preservation of the venous endothelium by <<dissection without touching>> and by an atraumatic technique of vascular anastomosis". Minerva Chirurgica, vol. 32. pp. 693-700 (1977).
Tarlovskaya et al., "Endoscopic Investigations for Determining Lung Cancer Stage" (1978).
Stiles, "Technique of Saphenous vein aorta-coronary bypass grafting", The Journal of Thoracic and Cardiovascular Sugery, vol. 78, No. 2, pp. 305-308 (Aug. 1979).
May et al., "Concluding Remarks on the Therapy of Incompetent Perforating Veins", Perforating Veins, pp. 251-253 (1981).
Szilagyi et al., "Autogenous vein grafting in femoropopliteal atherosclerosis: The limits of its effectiveness", Surgery, vol. 86, No. 6, pp. 836-851 (1979).
Flemma et al., "Complications of Aortocoronary Bypass Grafting", Complications of Intrathoracic Surgery, pp. 167-177 (1979).
Ochsner et al., "The Internal Mammary Artery as a Coronary Artery Bypass Graft", Coronary Heart Surgery, pp. 120-124 (1979).
Buxton et al., "The significance of vein wall thickness and diameter in relation to the patency of femoropopliteal Saphenous vein bypass grafts", Surgery, vol. 87, No. 4, pp. 425-431 (Apr. 1980).

Hofer et al., "Morphologic Studies in Saphenous Vein Grafts for Aorto-coronary Bypass Surgery Part 1: Morphology of the Graft Using Ordinary Surgical Preparation Techniques", The Thoracic and Cardiovascular Surgeon, vol. 29, No. 1, pp. 32-37 (1981).

Bonchek, "Prevention of endothelial damage during preparation of Saphenous veins for bypass grafting", The Journal of Thoracic and Cardiovascular Surgery, vol. 79. No. 6. pp. 911-915 (Jun. 1980).

McGeachie et al.. "Vein to Artery Grafts: A Quantitative Study of Revascularization by Vasa Vasorum and its Relationship to Intimal Hyperplasia", Annals of Surgery. vol. 194. No. 1. pp. 100-107 (Jul. 1981).

Gundry et al., "Intraoperative Trauma to Human Saphenous Veins: Scanning Electron Microscopic Comparison of Preparation Techniques", The Annals of Thoracic Surgery. vol. 30. No. 1. pp. 40-47 (Jul. 1980).

Buchbinder et al., "Comparison of Patency Rate and Structural Change in In Situ and Reversed Vein Arterial Bypass", Journal of Surgical Research, vol. 30. No. 3. pp. 213-222 (Mar. 1981).

Gundry et al., "Optimal preparation techniques for human Saphenous vein grafts", Surgery, vol. 88, No. 6, pp. 785-794 (Dec. 1980).

Moser, "Angioscopic Visualization of Pulmonary Emboli", Chest, vol. 77, No. 2, pp. 198-201 (Feb. 1980).

Ford et al., "Isolation of Adult Canine Venous Endothelium for Tissue Culture", In Vitro, vol. 17, No. 1, pp. 44-50 (Jan. 1980).

Delaria et al., "Leg wound complications associated with coronary revascularization", The Journal of Thoracic and Cardiovascular Surgery, vol. 81. pp. 403-407 (1981).

Fogarty et al.., "Adjunctive Intraoperative Arterial Dilation: Simplified Instrumentation Technique", Archives of Surgery, vol. 116. No. 11. pp. 1391-1398 (Nov. 1981).

Logerfo et al., "An improved technique for preservation endothelial morphology in vein grafts", Surgery, vol. 90, No. 6, pp. 1015-1024 (Dec. 1981).

Greenberg et al., "Vein-Donor-Leg Cellulities After Coronary Artery Bypass Surgery", Annals of Internal Medicine, vol. 97, No. 4, pp. 565-566 (Oct. 1982).

Gunstensen et al., "Intimal Hyperplasia in Autogenous Veins Used for Arterial Replacement", The Canadian Journal of Surgery, vol. 25. No. 2. pp. 158-165 (Mar. 1982).

McGoon, "Incision Decision Advertisement", The Journal of Thoracic and Cardiovascular Surgery, vol. 83, No. 5 (May 1982).

Catinella et al.., "The factors influencing early patency of coronary artery bypass vein grafts: Correlation of angiographic and ultrastructure findings", The Journal of Thoracic Cardiovascular Surgery, vol. 83, No. 5, pp. 686-700 (May 1982).

Feikes et al., "Harvesting and protection of the Saphenous vein associated with early delivery of blood cardioplegia in coronary artery bypass graft surgery", American Heart Journal, vol. 104. No. 2. Part 1, pp. 329-332 (1982).

Leather et al., "The In Situ Saphenous Vein for Arterial Bypass", Biologic and Synthetic Vascular Prostheses, pp. 351-364 (1982).

Sottiurai et al., "Autogenous Vein Grafts: Experimental Studies", Biologic and Synthetic Vascular Prostheses, pp. 311-364 (1982).

Kinney et al., "Transluminal Angioplasty: A Mechanical-Pathophysiological Correlation of its Physical Mechanisms", Radiology, vol. 153, No. 1, pp. 85-89 (Oct. 1984).

Teimourian et al., "Subcutaneous Endoscopy in Suction Lipectomy", Plastic and Reconstructive Surgery, vol. 74, No. 5, pp. 708-711 (Nov. 1984).

Gregory et al., "Composite Grafts: An Alternative to Saphenous Vein for Lower Extremity Arterial Reconstruction", The Journal of Cardiovascular Surgery, vol. 24. No. 1. pp. 53-57 (Jan.-Feb. 1983).

Hufnagel, "Chapter 1: History of Vascular Grafting", Vascular Grafting—Clinical Appliations and Techniques, pp. 1-12 (1983).

Shah et al., "In Situ Saphenous Vein Arterial Bypass", Vascular Grafting: Clinical Applications and Techniques, pp. 133-147 (1983).

Baddour et al., "Recurrent Cellulitis After Coronary Bypass Surgery", The Journal of the American Medical Journal, vol. 251. No. 8. pp. 1049-1052 (Feb. 17, 1984).

Chin et al., "A Physical Measurement of the Mechanisms of Transluminal Angioplasty", Surgery, vol. 95, No. 2, pp. 196-201 (Feb. 1984).

Crew et al., "Carotid Surgery without Angiography", The American Journal of Surgery, vol. 148, pp. 217-220 (Aug. 1984).

Adcock et al., "Optimal Techniques for Harvesting and Preparation of Reversed Autogenous Vein Grafts for Use as Arterial Substitutes: A Review", vol. 96, No. 5, (Nov. 1984).

Rashid et al., "Subcutaneous Technique for Saphenous Vein Harvest", The Annals of Thoracic Surgery, vol. 37, No. 2, pp. 169-170 (Feb. 1984).

Ben-Simhon et al., "Vein Harvesting by Long Blunt and Blind Dissection. A Standardized Technique in the Dog", Biomaterials, Medical Devices, and Artificial Organs, vol. 12, No. 1 & 2, pp. 51-66 (1984).

Dorsey, "Harvesting the Greater Saphenous Vein with a Subcutaneous Vein Remover", The Canadian Journal of Surgery, vol. 28, No. 1, pp. 13-14 (Jan. 1985).

Tilanus et al., "Saphenous Vein or PTFE for Femoropopliteal Bypass", Annals of Surgery, vol. 202, No. 6, pp. 780-782 (Dec. 1985).

Dorsey, "Saphenous Vein Harvesting Using a Subcutaneous Vein Remover", Minnesota Medical Association, pp. 195-198 (Mar. 1985).

Baddour, "Delayed Soft Tissue Infections in Saphenous Venectomy Limbs of Coronary Bypass Patients", Infections in Surgery, vol. 4, No. 4, pp. 243-248 (Apr. 1985).

Spears et al., "Coronary Angioscopy During Cardiac Catheterization", Journal of the American College of Cardiology, vol. 6. No. 1. pp. 93-97 (Jul. 1985).

Hulka et al., "Standard Gynecologic Techniques", Textbook of Laparoscopy, (1994).

Hobbs, "A New Approach to Short Saphenous Vein Varicosities", Surgery of Veins, pp. 301-321 (1985).

Nagovitsyn, "Operative Treatment of Acute Thrombophlebitis of the Superficial Veins of the Lower Extremities" (1985).

Weaver et al., "The Lesser Saphenous Vein: Autogenous Tissue for Lower Extremity Revascularization", Journal of Vascular Surgery, vol. 5, No. 5, pp. 687-692 (May 1987).

Scher et al., "Prevention and Management of Ischemic Complications of Vein Harvest Incisions in Cardiac Surgery Case Reports", Angiology, The Journal of Vascular Diseases, vol. 37, No. 1, pp. 119-123 (Jan. 1986).

Taylor et al., "Present Status of Reversed Vein Bypass for Lower Extremity", Journal of Vascular Surgery, vol. 3, No. 2, pp. 288-297 (Feb. 1986).

Meldrum-Hanna, "Long Saphenous Vein Harvesting", The Australian and New Zealand Journal of Surgery, vol. 56, No. 12, pp. 923-924 (Dec. 1986).

Raess et al., "Lesser Saphenous Vein as an Alternative Conduit of Choice in Coronary Bypass Operations", The Annals of Thoracic Surgery, vol. 41. No. 3, pp. 334-336 (Mar. 1986).

Sanborn, "Vascular Endoscopy: Current State of the Art", British Medical Bulletin, vol. 42, No. 3, pp. 270-273 (Apr. 1986).

Grundfest et al., "The Current Status of Angioscopy and Laser Angioplasty", Journal of Vascular Surgery, vol. 5, No. 4. pp. 667-673 (Apr. 1987).

Lemaitre et al., "In Situ Grafting Made Easy", Archives of Surgery, vol. 123, No. 1, pp. 101-103 (Jan. 1988).

Fleisher et al., "Angioscopically Monitored Saphenous Vein Valvulotomy", Journal of Vascular Surgery, vol. 4, No. 4, pp. 360-364 (Oct. 1986).

Miller, "Endoscopic Surgery of the Upper Urinary Tract", British Medical Bulletin, vol. 43, No. 3, pp. 274-279 (1986).

Nagovitsyn, "The Endoscopic Correction of the Shin Venous Blood Flow", Vestnik Khriurgii, vol. 137, No. 11, pp. 48-51 (Nov. 1986).

Noera et al., "Microscopic Evaluation in Saphenous Veins Used as Aortocoronary Bypass Grafts", Giornale Italiano di Cardiologia, vol. 16, No. 12, pp. 1037-1042 (Dec. 1986).

Suma et al. "Vein Perfusions System" for Harvesting the Saphenous Vein Graft in Coronary Bypass Surgery, Kyobu Geka, vol. 39. No. 8. pp. 622-623 (Aug. 1986).

Mehigan, "Symposium: Vascular Application of Angioscopy and Lasers", Journal of Vascular Surgery, vol. 5, No. 4, pp. 664-666 (Apr. 1987).

Taylor et al., "Autogenous Reversed Vein Bypass for Lower Extremity Ischemia in Patients with Absent of Inadequate Greater Saphenous Vein", The American Journal of Surgery, vol. 153, pp. 505-510 (May 1987).

Hashizume et al., "Intimal Response of Saphenous Vein to Intraluminal Trauma by Simulated Angioscope Insertion", Journal of Vascular Surgery, vol. 5, No. 6, pp. 862-868 (Jun. 1987).

Spyt, "Harvesting of the Lesser Saphenous Vein", The Annals of Thoracic Surgery, vol. 43, No. 6, p. 691 (Jun. 1987).

White, "Angioscopy and Laser in cardiovascular Surgery: Current Applications and Future Prospects", Aust. N. Z. J. Surg., vol. 58. No. 271-274 (1988).

Matsumoto et al., "Direct Vision Valvulotomy in In Situ Venous Bypass", Surgery Gynecology & Obstetrics, vol. 165, No. 4 (Oct. 1987).

Classen et al., "Electronic Endoscopy—The Latest Technology", Endoscopy, vol. 19, pp. 118-123 (1987).

Delmotte, "The Electronic Video Endoscope of Tomorrow, but First, its Present Status", Acta Endoscopica, vol. 17, No. 2, pp. 89-91 (1987).

Dimitri et al., "A Quick and Atraumatic Method of Autologous Vein Harvesting Using the Subcutaneous Extraluminal Dissector", The Journal of Cardiovascular Sugery, vol. 28, No. 2, pp. 103-111 (Mar.-Apr. 1987).

Secroun, "Future Methods of Endoscopy", Acta Endoscopica, vol. 17, No. 2, pp. 92-95 (1987).

Lannerstad et al., "Effects of Different Graft Preparation Techniques on the Acute Thrombogenicity of Autologous Vein Grafts", European Surgical Research, vol. 19, pp. 395-399 (Nov.-Dec. 1987).

Towne, "Vascular Endoscopy", Perioperative Assessment in Vascular Surgery, pp. 303-313 (1987).

Chin et al., "The Effect of Valvulotomy on the Flow Rate Through the Saphenous Vein Graft: Clinical Implications", Journal of Vascular Surgery, vol. 8, No. 3, pp. 316-320 (Sep. 1988).

Wood, "Locating Previously "Stripped" Venous Systems and Harvesting of Lesser Saphenous Vein", The Annals of Thoracic Surgery, vol. 45, No. 3 (Mar. 1988).

Takemoto, "Electronic Endoscopy: Its Present and Future", Journal of Gastroenterology and Hepatology, vol. 4, pp. 75-80 (1989).

Cardella et al., "Lower-Extremity Venous Thrombosis: Comparison of Venography, Impedance Plethysmography, and Intravenous Manometry", Radiology, vol. 168. No. 1, pp. 109-112 (Jul. 1988).

Citrin et al., "Replacement of the Carotid Artery Using Nonreversed Saphenous Vein", Surgery, Gynecology & Obstetrics, vol. 167, pp. 155-157 (Aug. 1988).

Woelfle et al., "Intraoperative Assessment of In Situ Saphenous Vein Bypass Grafts by Vascular Endoscopy", European Journal Vascular Endovascular Surgery European, vol. 2, pp. 257-262 (Aug. 1988).

Patel et al., "The Use of Fiber-Optic Intraluminal Transillumination for Saphenous Vein Harvesting", Journal of Vascular Surgery, vol. 8, No. 3, pp. 346-348 (Sep. 1988).

Gaudiani et al., "An Improved Technique for the Internal Mammary Artery Coronary Bypass Graft Procedure", Journal of Cardiac Surgery, vol. 3, No. 4, pp. 467-473 (Dec. 1988).

Hauer et al., "Endoscopic Subfascial Dissection of Perforating Veins", Surgical Endoscopy, vol. 2, pp. 5-12 (1988).

Lee et al., "Hazards of Angioscopic Examination: Documentation of Damage to the Arterial Intima", American Heart Journal, vol. 116, No. 6, pp. 1530-1536 (Dec. 1988).

Rey et al., "Electronic Video Endoscopy: Preliminary Results of Imaging Modification", Endoscopy, vol. 20, pp. 8-10 (1988).

Taylor et al., "Reversed vs. In Situ: Is Either the Technique of Choice for Lower Extremity Vein Bypass?", Perspectives in Vascular Surgery, vol. 1, No. 1, pp. 35-59 (1988).

Barnes et al., "Technical Innovations in Nonreversed Translocated Saphenous Vein Bypass", Journal of Vascular Surgery, vol. 9, No. 3, pp. 499-501 (Mar. 1989).

Chin et al., "Technique Using the Fiberoptic Valvulotome for the In Situ Vein Graft", Surgery Gynecology & Obstetrics, vol. 169, No. 3, pp. 255-256 (Sep. 1989).

Hauer, "Diagnosis and surgical management of varicosities", Herz, vol. 14, No. 5, pp. 274-282 (1989).

Fogarty et al., "Combined Thrombectomy and Dilation for the Treatment of Acute Lower Extremity Arterial Thrombosis", Journal of Vascular Surgery, vol. 10, No. 5, pp. 531-534 (Nov. 1989).

Burnand, "Reversed Saphenous Vein for Femoropopliteal Bypass Grafting", Vascular Surgical Techniques An Atlas, pp. 228-234 (1989).

Chin et al., "Angioscopic Preparation for Saphenous Vein In Situ Bypass Grafting", Endovascular Surgery, pp. 74-81 (1989).

Lavee et al., "Complications of Saphenous Vein Harvesting Following Coronary Artery Bypass Surgery", The Journal of Cardiovascular Surgery, vol. 30, No. 6, pp. 989-991 (1989).

Utley et al., "Preoperative Correlates of Impaired Wound Healing After Saphenous Vein Excision", The Journal of Cardiovascular Surgery, vol. 98, No. 1, pp. 147-149 (1989).

Veith et al., Short Vein Grafts in Limb-saving Arterial Reconstructions, Journal of Vascular and Interventional Radiology, vol. 1, No. 1, pp. 57-61 (Nov. 1990).

Louagie et al., "Viability of Long-Term Cryopreserved Human Saphenous Vein", The Journal of Cardiovascular Surgery, vol. 31, No. 1, pp. 92-100 (Jan.-Feb. 1990).

Galloway, Jr. et al., "A new Device for Interactive, Image-Guided Surgery", Medical Imaging V: Image Capture, Formatting, and Display, SPIE-The International Society of Optical Engineering (Feb. 1991).

Myers et. al., "Semi-closed, ex-situ, non-reversed or reversed autogenous vein grafting", The Journal of Cardiovascular Surgery, vol. 32. No. 1. pp. 110-116 (Jan.-Feb. 1991).

Bailey et al., "Laparoscopic Cholecystectomy: Experience with 375 Consecutive Patients", Ann. Surg., vol. 214, No. 4, pp. 531-540 (1991).

The Southern Surgeons Club, "A Prospective Analysis of 1518 Laparoscopic Cholecystectomies", New England Journal of Medicine, vol. 324, pp. 1073-1078 (Apr. 18, 1991).

Clayman et al.., "Laparoscopic Nephrectomy", The New England Journal of Medicine, vol. 324, No. 19, pp. 1370-1371 (May 9, 1991).

Lam, et al., "Surgical Procedures for Uncomplicated ("Routine") Female Stress Incontinence", The Urologic Clinics of North America, vol. 18, No. 2, pp. 327-337 (May 1991).

Couto et al., "Endoscopic ligation of perforator leg veins", The Lancet, vol. 337, p. 1480 (Jun. 15, 1991).

Milgalter et al., "A technique to harvest the inferior epigastric arteries for coronary bypass procedures", Journal of Cardiac Surgery, vol. 6, No. 2, pp. 306-310 (Jun. 1991).

Preising et al., "A Literature Review: Robots in Medicine", _Engineering in Medicine and Biology (Jun. 1991).

Owen et al., "Endoscopic ligation of perforator leg veins", Lancet, vol. 338, p. 248 (Jul. 27, 1991).

McCollum et al., "A Simple Means of Access for Harvesting the Lesser Saphenous Vein", European Journal Vascular Endovascular Surgery, vol. 5, pp. 469-470 (Aug. 1991).

Feldman, "Laparoscopic Nephrectomy", Journal of Medicine, vol. 325, No. 15, pp. 1110-1111 (Oct. 10, 1991).

Nowzaradan et al., "Laparoscopic Appendectomy for Acute Appendicitis: Indications and Current Use", Journal of Laparoendoscopic Surgery, vol. 1, No. 5. pp. 247-257 (Oct. 1991).

Spaw et al., "Laparoscopic Hernia Repair: The Anatomic Basis", Journal of Laparoendoscopic Surgery, vol. 1, No. 5, pp. 269-277 (Oct. 1991).

Stierli et al., "In Situ Femorodistal Bypass: Novel Technique for Angioscope-Assisted Intraluminal Side-Branch Occlusion and Valvulotomy. A preliminary Report", British Journal of Surgery, vol. 78, No. 11, pp. 1376-1378 (Nov. 1991).

Bailey et al., "Combined Laparoscopic Cholecystectomy and Selective Vagotomy", Surgical Laparoscopy & Endoscopy, vol. 1, No. 1, pp. 45-49 (1991).

Bergamini et al., "Experience with in situ saphenous vein bypass during 1981 to 1989:Determinant factors of long-term patency". p. 137 (1991).

Corbitt, Jr., "Laparoscopic Herniorrhaphy", Surgical Laparoscopy & Endoscopy, vol. 1, No. 1, pp. 23-25 (1991).

Cuschieri, "Variable curvature shape-memory spatula for laparoscopic surgery", Surgical Endoscopy, vol. 5, pp. 179-181 (1991).

Fitzgibbons et al., "Open Laparoscopy", Surgical Laparoscopy, pp. 87-97 (1991).
Fowler et al.., "Laparoscopy-Assisted Sigmoid Resection", Surgical Laparoscopy & Endoscopy, vol. 1, No. 3, pp. 183-188 (1991).
Gazayerli, "The Gazayerli Endoscopic Retractor Model 1" Surgical Laparoscopy & Endoscopy, vol. 1, No. 2, pp. 98-100 (1991).
Zhila et al., "High Resection of the Left Testicular Vein and Ligation of the Internal Iliac Arteries by Means of Retroperitoneoscope", No. 5 (1991).
Zucker, "Laparoscopic Guided Cholecystectomy With Electrocautery Dissection", Surgical Laparoscopy, pp. 143-182 (1991).
"3rd World Congress of Endoscopic Surgery" (Jun. 18-20, 1992).
Santilli et al., "Comparison of Preoperative Standard Angiography with Preoperative Balloon Occlusion Femoral Angiography of the Lower Extremity", Journal of Investigative Surgery, vol. 6, No. 1, pp. 83-95 (Feb. 1993).
Zucker, Surgical Laparoscopy Update, pp. 59-61 (1993).
Wittens et al., "A New "Closed" In Situ Vein Bypass Technique", European Journal Vascular Endovascular Surgery, vol. 8, pp. 166-170 (1994).
Biglioli et al., "Arterial and Venous Graft Utilization in Reoperative Coronary Artery Surgery", Cardiology and Cardiac Surgery: Current Topics, pp. 399-415 (1993).
Chin et al., "Novel Technique and Instrumentation for Laparoscopic Application of Hemostatic Clips", The Journal of the American Association of Gynecologic Laparoscopists, vol. 1, No. 2, pp. 150-153 (Feb. 1994).
Chin et al., "Gasless Laparoscopy Using a Planar Lifting Technique", Journal of the American College of Surgeons, vol. 178. No. 4, pp. 401-403 (Apr. 1, 1994).
Kavoussi et al., "Telerobotic Assisted Laparoscopic Surgery: Initial Laboratory and Clinical Experience", Urology, vol. 44, No. 1, pp. 15-19 (Jul. 1994).
Van Dijk et al., "A New "Closed" In Situ Vein Bypass Technique Results in a Reduced Wound Complication Rate", European Journal Vascular Endovascular Surgery, vol. 10, pp. 162-167 Aug. 1995).
Lumsden et al., "Subcutaneous, Video-Assisted Saphenous Vein harvest: Report of the first 30 Cases", Cardiovascular Surgery, vol. 4, No. 6, pp. 771-776 (Dec. 1996).
Tighe, Instrumentation for the Operating Room: A Photographic Manual (1994).
Dion et al., "Experimental Iaparoscopic aortobifemoral bypass", Surgical Endoscopy, vol. 9, pp. 894-897 (1995).
Bowersox et al., "Vascular applications of telepresence surgery: Initial feasibility studies in swine", Journal of Vascular Surgery, vol. 23, No. 2., pp. 281-287 (Feb. 1996).
Rosenthal, "Endoscopic in Situ Bypass", The Surgical Clinics of North America, vol. 75, No. 4, pp. 703-713 (Aug. 1995).
Nwasokwa et al., "Coronary Artery Bypass Graft Disease", Annals of Internal Medicine, vol. 123, No. 7, pp. 528-545 (Oct. 1995).
Davies et al., "Pathophysiology of Vein Graft Failure: A Review", European Journal Vascular Endovascular Surgery, vol. 9, pp. 7-18 (1995).
Gelijns et al., "From the Scalpel to the Scope: Endoscopic Innovations in Gastroenterology, Gynecology, and Surgery", Sources of Medical Technology: Universities and Industry, vol. V, pp. 67-96 (1995).
Lumsden et al., "Vein Harvest", Endoscopic Plastic Surgery (1995).
Sawaizumi et al., "Endoscopic Microsurgical Anastomosis: Experimental Study of microsurgical anastomosis using an endoscope", Journal of Japan Society of Plastic and Reconstructive Surgery, vol. 15. No, 12, pp. 871-879 (1995).
Tebbetts, Tebbetts Endoplastic Instrument System (1995).
Cusimano, "Minimally Invasive Cardiac Surgery for Removal of the Greater Saphenous Vein", Canadian Journal of Surgery, vol. 39 (Oct. 1996), http://www.cma.ca/index.cfm/ci.
Tevaearai et al., "Minimally Invasive Harvest of the Saphenous Vein for Coronary Artery Bypass Grafting", The Annals of Thoracic Surgery, vol. 63, pp. S119-S121 (1997).
Iafrati et al., "Endoscopic in situ bypass: A gentler dissection", Surgical Endoscopy, vol. 12, pp. 463-465 (1998).

Hannah et al., "Laparoscopic Retropubic Urethropexy", The Journal of the American Association of Gynecologic Laparoscopists, vol. 4, No. 1, pp. 47-52 (Nov. 1996).
EndoCABG System: Innovative instrumentation for endoscopic coronary artery bypass grafting (1996).
Lumsden et al., "Subcutaneous, video-assisted saphenous vein harvest", Perspectives in Vascular Surgery, vol. 7, No. 2, pp. 43-55 (1994).
Allen et al., "Endoscopic Saphenous Vein Harvesting", pp. 265-266 (1997).
McCarthy et al., "Tricuspid Valve Repair with the Cosgrove-Edwards Annuloplasty System", The Annals of Thoracic Surgery, vol. 64, pp. 267-268 (1997).
Jordan et al., "Video-assisted saphenous vein harvest: The evolution of a new technique", Journal of Vascular Surgery, vol. 26, No. 3, pp. 405-414 (Sep. 1997).
Moazami, "Minimally Invasive Greater Saphenous Vein Harvesting for Coronary Artery Bypass Surgery", Surgical Rounds, pp. 94-98 (Mar. 1997).
Johnson et al., "Endoscopic Femoral-Popliteal/Distal Bypas Grafting: A Preliminary Report", Journal of American College of Surgeons, pp. 331-336 (1998).
Pierik et al., "Endoscopic versus open subfacial division of incompetent perforating veins in the treatment of venous leg ulceration: A randomized trial", Journal of Vascular Surgery, vol. 26, No. 6, pp. 1049-1054 (1997).
Davis et al., "Endoscopic Vein Harvest for Coronary Artery Bypass Grafting: Technique and Outcomes", The Journal of Thoracic and Cardiovascular Surgery, vol. 116, No. 2, pp. 228-235(Aug. 1998).
Hallock et al., "An Endoscopic Subcutaneous Dissector for Obtaining Vein Grafts", Annals of Plastic Surgery, vol. 41, No. 6, pp. 595-599 (Dec. 1998).
Morris et al., "Minimally Invasive Saphenous Vein Harvesting", The Annals of Thoracic Surgery, vol. 66, pp. 1026-1028 (1998).
Allen et al., "Endoscopic Versus Traditional Saphenous Vein Harvesting: A Prospective, Randomized Trial", pp. 26-31 (1998).
Stavridis et al., "Minimally Invasive Long Saphenous Vein Harvesting Using a Laryngoscope", The Heart Surgery Forum, vol. 1, pp. 37-40 (Jan. 30, 1998).
Tran et al., "Tunneling versus open harvest technique in obtaining venous conduits for coronary bypass surgery", European Journal of Cardo-thoracic Surgery, vol. 14, pp. 602-606 (1998).
Wilson, "Ethicon Endopath System", Minimally Invasive Vein Harvesting The Second Generation (Jun. 1998).
"Resins Aid in Bypass Surgery", Plastics Engineering, vol. LIV, No. 8 (Aug. 1998).
Dregelid et al., "Endothelial cell injury in human saphenous veins after manipulation and tweezer grasping", Journal of Cardiovascular Surgery, vol. 29, pp. 464-469 (1988).
Voellinger et al., "Video-Assisted Vein Harvest: A Single Institution's Experience of 103 Peripheral Bypass Cases", Vascular Surgery, vol. 32, No. 6, (Nov./Dec. 1998).
Akbari et al., "Saphenous Vein Bypass to Pedal Arteries in Diabetic Patients", pp. 227-232 (1998).
Belkin et al., "Nonreversed Saphenous Vein Bypass for Infrainguinal Arterial Reconstruction", Techniques in Vascular and Endovascular Surgery, pp. 233-241 (1998).
Kulbaski et al., "Video-Assisted Saphenous Vein Harvest", Techniques in Vascular and Endovascular Surgery, pp. 91-102 (1998).
Kyo et al., "Endoscopic harvest of saphenous vein graft for coronary artery bypass grafting: Saitama—Olympus technique", European Journal of Cardio-thoracic Surgery, vol. 14, Suppl, 1, pp. S94-S99 (1998).
Lacroix et al., "Classic versus Endoscopic Perforating Vein Surgery:a Retrospective Study", Acia chir bieg, vol. 98, pp. 71-75 (1998).
Stoney et al., "Lower Extremity", Comprehensive Vascular Exposures, pp. 145-182 (1998).
Brown et al., "Heparin Reduced Residual Clot Within the Lumen of Endoscopically Harvested Saphenous Veins", http://www.aats.org/annualmeeting/Abstracts/2007/T7.html (Aug. 6, 2008).
Snowden-Pencer, Inc., "Emory Endoplastic Instruments", Endoscopic Plastic Surgery, pp. 1-10 (1993).

Wengrovitz, "Wound Complications of Autogenous Subcutaneous Infrainguinal Arterial Bypass Surgery: Predisposing Factors and Management", vol. 11, No. 1, pp. 156-163 (Jan. 1990).
Iafrati, "Laparoscopic Cholecystectomy in the Community Hospital, our first 101 cases", Current Surgery, vol. 48, No. 10 (Dec. 1991).
Ashby, "Operative Choledochoscopy in Common Bile Duct Surgery", Annals of the Royal College of Surgeons of England, vol. 67, pp. 279-283 (1985).
Nezhat et al., "Salpingectomy via Laparoscopy: a new surgical approach" Journal of Laparoendoscopic Surgery (1991), http://www.ncbi.nlm.nih.gov/pubmed/1834264.
Gershman et al., "Laparoscopic Pelvic Lymphadenectomy", Journal of Laparoendoscopic Surgery, vol. 1, No. 1 (1990).
Leahy et al., "Minimally Invasive Esophagogastrectomy: An Approach to Esophagogastrectomy Through the Left Thorax", Journal of Laparoendosopic Surgery, vol. 1, No. 1, pp. 59-62 (Nov. 1990).
Towbin et al., "Real-Time US Guidance During Renal Biopsy in Children", Journal of Vascular and Interventional Radiology (1991), http://www.ncbi.nlm.nih.gov/pubmed/1797225.
Cooperman et al.., "Laparoscopic Colon Resection: a case report", J. Laparoendoscopic Surgery 1991, http://www.ncbi.nlm.nih.gov/pubmed/1834273.
Gunther, "Percutaneous Interventions in the Thorax", Journal of Vascular and Interventional Radiology, pp. 379-390 (May 1992).
Zuckerman et al., Splenopneumopexy: evaluation with splenoportography, Journal of Vascular and Interventional Radiology, vol. 3, No. 1 (Feb. 1992), http://www.ncbi.nlm.nih.gov/pubmed/1540718.
Tyler, "Voluntary Sterilization", American Journal of Public Health, vol. 63, No. 7, pp. 573-575 (Jul. 1973).
Yeager et al., "Surgical Management of Severe Acute Lower Extremity Ischemia", Journal of Vascular Surgery, vol. 15, No. 2, pp. 385-393 (Feb. 1992).
Woelfle et al., "Technique and Results of Vascular Endoscopy in Arterial and Venous Reconstructions", Annals of Vascular Surgery, vol. 6, No. 4, pp. 347-356 (Jul. 1992).
Stierli et al., "Angioscopy-guided semiclosed technique for in situ bypass with a novel flushing valvulotome: Early results", Journal of Vascular Surgery, vol. 15, No. 3, pp. 564-568 (Mar. 1992).
Stahlfeld et al., "Letter to the editor: A simple technique to protect subcutaneous grafts", Journal of Vascular Surgery, p. 1080 (Jun. 1992).
Shah et al., "Is long vein bypass from groin to ankle a durable procedure? An analysis of a ten-year experience", Journal of Vascular Surgery, vol. 15 (1992).
Rosenthal et al., "Endovascular infrainguinal in situ saphenous vein bypass: A multicenter preliminary report", Journal of Vascular Surgery, vol. 16 (1992).
Pietrafitta et al., "An Experimental Technique of Laparoscopic Bowel Resection and Reanastomosis", Surgical Laparoscopy & Endoscopy, vol. 2, No. 3, pp. 205-211 (Sep. 1992).
Pier et al., "Laparoscopic Appendectomy in 625 Cases: From Innovation to Routine", Surgical Laparoscopy & Endoscopy, vol. 1, No. 1 pp. 8-13 (1991).
Pearce et al., "The Use of Angioscopy in the Saphenous Vein Bypass Graft", Technologies in Vascular Surgery, pp. 289-294 (1992).
Narayanan et al., "Experimental Endoscopic Subcutaneous Surgery", Journal of Laparoendoscopic Surgery, vol. 2, No. 3. pp. 179-183 (1992).
McPherson et al., "Intravascular Ultrasound: Principles and Techniques", Technologies in Vascular Surgery, pp. 233-241 (1992).
Jugenheimer et al., "Endoscopic Subfascial Sectioning of Incompetent Perforating Veins in Treatment of Primary Varicosis", World Journal of Surgery, vol. 16. pp. 971-975 (1992).
Harward et al., "The use of arm vein conduits during infrageniculate arterial bypass", Vascular Surgery (1992).
Flinn et al., "A comparative study of angioscopy and completion arteriography after infrainguinal bypass", Tehcnologies iin Vascular Surgery, pp. 295-305 (1992).
Dries et al., "The Influence of Harvesting Technique on Endothelial Preservation in Saphenous Veins", Journal of Surgical Research, vol. 52, No. 3, pp. 219-225 (Mar. 1992).

Taylor et al., "Technique of Reversed Vein Bypass to Distal Leg Arteries", Techniques in Arterial Surgery, pp. 109-122 (1990).
Taylor et al., "Present status of reversed vein bypass grafting: Five-year results of a modern series", Journal of Vascular Surgery, vol. 11, No. 2, pp. 193-206 (Feb. 1990).
Schmidt et al., "A Canine Model of Intimal Hyperplasia (IH) in Autogenous Vein Grafting: A Preliminary Report", Journal of Investigative Surgery, vol. 3, No. 4, pp. 357-364 (1990).
Sadick, "Treatment of Varicose and Telagiectatic Leg Veins with Hypertonic Saline: A Comparative Study of Heparin and Saline". The Journal of Dermatologic Surgery and Oncology, vol. 16, No. 1, pp. 24-28 (Jan. 1990).
Sadick, "Sclerotherapy of Varicose and Telangiectatic Leg Veins: Minimal Sclerosant Concentration of Hypertonic Saline and Its Relationship to Vessel Diameter", The Journal of Dermatologic Surgery and Oncology, vol. 17, pp. 65-70 (1991).
Lamuraglia et al., "Angioscopy guided semiclosed technique for in situ bypass", Journal of Vascular Surgery, vol. 12, No. 5, pp. 601-604 (Nov. 1990).
Knighton et al., "Saphenous Vein In Situ Bypass", The American Journal of Surgery, vol. 160, pp. 294-299 (Sep. 1990).
Feinberg et al., "The use of composite grafts in femorocrural bypasses performed for limb salvage: A review of 108 consecutive case and comparison with 57 in situ saphenous vein bypasses", Journal of Vascular Surgery (1990).
Beretta et al., "Gastroepiploic artery free graft for coronary bypass", European Journal of Cardiothoracic Surgery, vol. 4. pp. 323-328 (1990).
Troidl, "Surgical Endoscopy and Sonography", Surgical Endoscopy, vol. 4, pp. 41-46 (1990).
Cotton, "Biomedical Engineering in Vascular Surgery", Annals of the Royal College of Surgeons of England, vol. 54, pp. 22-32 (1974).
Crispin, "Arterial Endoscopy", Acta Chirurgica Belgica, No. 1, pp. 59-67 (Jan. 1974).
Plecha, "An Improved Method of Harvesting Long Saphenous Vein Grafts", Archives of Surgery, vol. 108, No. 1 (Jan.-Jun. 1974).
Vollmar et al., "Vascular Endoscopy", The Surgical Clinics of North America, vol. 54, No. 1, pp. 111-122 (Feb. 1974).
Fogarty, "Combined thrombectomy and dilation for the treatment of acute lower extremity arterial thrombosis", Journal of Vascular Surgery, vol. 10, No. 4, 530-534 (Oct. 1989).
Blanco, "Resins Aid in Bypass Surgery", Plastics Engineering (Aug. 1998).
O'Neill, "The Effects on Venous Endothelium of Alterations in Blood Flow Through the Vessels in Vein Walls, and the Possible Relation to Thrombosis". Annals of Surgery, vol. 126. No, 3. pp. 270-288 (Sep. 1947).
Matsumoto et al., "Direct Vision Valvulotomy for Nonreversed Vein Graft", Sugery Gynecology & Obstetrics, vol. 165, No. 2, pp. 180-182 (1987).
Hauer, "Surgery of Perforating Veins", Langenbecks Archive Chirurgie Supplement, pp. 464-465 (1992).
Pierik et al., "Subfascial Endoscopic Ligation in the Treatment of Incompetent Perforating Veins", European Journal Vascular Endovascular Surgery, vol. 9, pp. 38-41 (1995).
Gottlob, "Reconstruction of Venous Valves", Venous Valves: Morphology Function Radiology Surgery, pp. 188-213 (1986).
Berci, "Techiques for improving illumination and recording in endoscopy", Optics and Laser Technology, pp. 31-37 (Feb. 1976).
Berci, Endoscopy today and tomorrow (1976).
Shumacker, "Weglowski's Pioneering Vascular Surgery and Barriers to Progress", Current Critical Problems in Vascular Surgery, vol. 3 (1991).
Buchbinder et al., "B-mode Ultrasonic Imaging in the Preoperative Evaluation of Saphenous Vein", The American Journal, vol. 53, No. 7, pp. 368-372 (Jul. 1987).
Hoffmann, "Die subfasziale, endosopische Laser-Perforantes-Dissektion unter Berucksichtigung auch der lateralen Perforansvenen", Vasomed, vol. 9, No. 5 (1997).
Fischer, "Eine neue Generation der Varizenchirurgie", VASA, Band 20, pp. 311-318 (1991).
Jugenheimer et. al., "Ergebnisse der endoskopischen Perforans-Dissektion", Der Chirung, pp. 625-628 (Aug. 1991).

Kern et al, "Technique of coronary angioscopy" (2008), http://www.uptodate.com/patients/content/topic.do.

Frazee, "Neuroendoscopy Program" (2008), http://neurosurgery.ucla.edu/body.cfm.

Berci et al., "History of Endoscopy", Surgical Endoscopy, vol. 14, pp. 5-15 (2000).

"Ultrasound and Interventional Techniques", Surgical Endoscopy, vol. 10, No. 1 (Jan. 1996).

"Minimal Invasive Surgery", Surgical Endoscopy: Ultrasound and Interventional Techniques, vol. 10, No. 1 (Jan. 1996).

"The Eyes of the Wolf are Sharper", Surgical Endoscopy: Ultrasound and Interventional Techniques, vol. 10, No. 3 (Mar. 1996).

"Endoscopic suturing made easy", Surgical Endoscopy: Ultrasound and Interventional Techniques, vol. 9, No. 2 (Feb. 1995).

"Instruments for percutaneous nucleotomy and discoscopy", Surgical Endoscopy: Ultrasound and Interventional Techniques, vol. 3, No. 1 (1995).

"Fiberscope for vascular endoscopy", Surgical Endoscopy: Ultrasound and Interventional Techniques, vol. 3, No. 2 (1989).

"Narrow operative approach, atraumatic examination. The Karl Storz Neuro-Endoscope", Surgical Endoscopy vol. 3, No. 3 (1989).

"Fiberscope for vascular endoscopy", Surgical Endoscopy vol. 3, No. 4 (1989).

"New: Universal-Neuro-Endoscope. New application possibilities for Neurosurgery", Surgical Endoscopy vol. 4, No. 1 (1990).

Springer book advertisement, Surgical Endoscopy vol. 4, No. 4 (1990).

Richard Wolf advertisement, Surgical Endoscopy, vol. 5, No. 1 (1991).

"Why do open surgery", Surgical Endoscopy, vol. 5, No. 2 (1991).

"Minimally invasive surgery. Operating proctoscope for anal surgery", Surgical Endoscopy, vol. 5, No. 3 (1991).

"Laparoscopic Surgery . . . The Next Generation", Surgical Endoscopy, Vo. 6, No. 2 (1992).

"There's a Revolution in Surgery. USSC was there in the beginning", Surgical Endoscopy, vol. 6, No. 3 (1992).

"Cuschieri Thoracoscopic Instruments", Surgical Endoscopy, vol. 6, No. 4 (1992).

"Laparoscopic has just turned a new corner . . . ", Surgical Endoscopy, vol. 6, No. 5 (1992).

"Electronic Video Laparoscopy", Surgical Endoscopy, vol. 6, No. 6 (1992).

"Performing a Nissen just got easier, faster, and cheaper", Surgical Endoscopy, vol. 9, No. 9 (1995).

"Easy entry . . . maximizes safety . . . ", Surgical Endoscopy, vol. 9, No. 5 (1995).

"Richard-Allan Medical Has Just Bent the Rules on Endoscopic Cutting", Surgical Endoscopy, vol. 10, No. 9 (1996).

"High quality endoscopic instruments", Surgical Endoscopy, vol. 10, No. 11 (1996).

"Endoscopic Surgery of the Paranasal Sinuses and Anterior Skull Base", Endoscopy, vol. 22, No. 5 (1990).

"Karl Storz—Endoscopes for bronchoscopy", Endoscopy, vol. 23, No. 1 (1991).

"Original Karl-Storz. System Perfection", Endoscopy, vol. 23, No. 3 (1991).

"Minimally invasive surgery.Laparascopic cholecystectomy", Endoscopy, vol. 23, No. 4 (1991).

"Greater Visibility, Lighter Weight", Endoscopy, Vo. 23, No. 5 (1991).

"A Different View on Diagnosis: (Toshiba Medical Systems) and 2 Live International Therapeutic Endoscopy Course in Mexico City Oct. 10-12, 1990", Endoscopy, vol. 22, No. 3 (1990).

ProMIS Line: The complete endoscopy program from AESCULAP, Endoscopy, vol. 28, No. 3 (1996).

"Now you can afford to change your point of view", Endoscopy, vol. 27, No. 3 (1995).

"Karl Storz endoscopes for NEODYM-YAG and C02 lasers", E 1990, Endoscopy, vol. 22, No. 1 (1990).

"Endoscopic Ultrasonography: EUS", Endoscopy, vol. 22, No. 2 (1990).

Surgical Laparoscopy & Endoscopy, vol. 1 No. 1 (1991).
Surgical Laparoscopy & Endoscopy, vol. 1, No. 2 (1991).
Surgical Laparoscopy & Endoscopy, vol. 1, No. 3 (1991).
Surgical Laparoscopy & Endoscopy, vol. 1, No. 4 (1991).
Surgical Laparoscopy & Endoscopy, vol. 2, No. 1 (1992).
Surgical Laparoscopy & Endoscopy, vol. 2, No. 2 (1992).
Surgical Laparoscopy & Endoscopy, vol. 2, No. 3 (1992).
Surgical Laparoscopy & Endoscopy, vol. 2, No. 4 (1992).

"Karl Storz Take-apart: the fully cleanable cost-effective, modular instrument solution", Surgical Laparoscopy & Endoscopy, vol. 6, No. 1 (1996).

Cuschieri, "How I Do It", Laparoscopic cholecystectomy (Mar. 1999).

"History of Endoscopy" (2008), http://wwww.alexea.org/.

"Laparoscopy" (1998), http://www.ehealthmd.com/library/laparoscopy/LAP_whatis.html.

White et al., Coronary Angioscopy, vol. 22, No. 1, pp. 20-25 (1995).

Olympus Endoscopic Accessories Price List, Effective Feb. 15, 1986.

Feldman, "Laparoscopic Nephrectomy", The New England Journal of Medicine, vol. 325, No. 15, pp. 1110-1111 (Oct. 10, 1991).

Kunlin, "Le traitement de l'ischámie arteritique pas la greffe veineuse longue", Revue de Chirurgie, pp. 206-235 (Aug. 1951).

Stanley et al. Autogenous Saphenous Vein as an Arterial Graft-Clinical Status in Stanley JC (ed): Biologic and Synthetic Vascular Prostheses, New York, Gmne and Stratton, Inc. 333-349 (1982).

Cohen et al Indications for Left Ventricular Aneurysmectomy *Circulation* 1983; 67; 717-722.

Evdokimov et al., "A Combination of Electroacupuncture and Conduction Anesthesia in Operations for Varicose Dilatation of Lower Extremity Veins", ISSN 0042-4625 (1985).

Lofgren Treatment of Long Saphenous Varicosities and Their Recurrence:A Long-Term Follow-Up, Surgery of the Veins, Grune & Stratton (1985).

Meldrum-Hanna et al. An Improved Technique for Long Saphenous Vein Harvesting for Coronary Revascularization, Annals of Thoracic Surgery 1986 42: 90-92.

Gottlob et al. Replacement of Small Veins by Autologous Grafts: Application of an Endothelium-Preserving Technique, *Vasc Endovascular Surg*, 1982: 16: 27 Vienna and New York.

Lukomskii, "Prevention of Post" (1986).

Nagovitsyn, "Endoscopic Coagulation of the Communicating Veins of the Leg in Chronic Venous Insufficiency", Sovetskaia Meditsina, vol. 12, pp. 109-110 (1987).

Buchbinder et al. B-Mode Ultrasonic Imaging in the Preoperative Evaluation of Saphenous Vein, American Surgeon, Jul. 1987, vol. 53, No. 7.

Sottiurari et al. Autogenous Vein Grafts:Experimental Studies, in Stanley JC (ed): Biologic and Synthetic Vascular Prostheses, New York, Gmne and Stratton, Inc. 311-331 (1982).

Hauer, "Operationstechnik der Endoskopischen Subjascialen Discision der Perforansvenen", Chirurg, vol. 58, pp. 172-175 (1987).

Nagovitsyn, "Endoscopic Electrocoagulation of the Communicating Crural Veins", Khirurgiia (Mosk), vol. 12, pp. 60-61 (Dec. 1987).

Secroun, "Future Methods of Endoscopy", Acta Endoscopica, vol. 17, No. 2, pp. 92-95 (1987).

Devambez et al., "Ecarteur Autostatique Pour Chirurgie de Varices", Phlebologie: Bulletin de la Societe Francaise de Phleaologie (1988).

Nagovitsyn, "Vein-sparing operations combined with endoscopic electrocoagulation of the communicating veins", Vestnik Khirurgii, vol. 140, No. 3, pp. 92-93 (Mar. 1988).

Nagovitsyn, "Prevention of complications for endoscopic correction of the crural venous blood flow", Vestnik Khirurgii, vol. 142, No. 3, pp. 113-115 (Mar. 1989).

Bailey et al., "Laparoscopic Cholecystectomy: Experience with 375 Consecutive Patients", Ann. Surg. (Oct. 1991).

Maignien, "Splénectomie par voie coelioscopique 1 observation", La Presse Médicale (Dec. 21-28, 1991).

Moll, "Historische Anmerkungen zur Entwicklung von Endoskopie and minimal invasiver Operations-technik", Geschichte der Medizin (1993).

Markstrom, "Intraoperativ angioskopi via infrainguinal bypass med vena saphena magna in situ", Medicinsk Rapport, vol. 89, No. 49 (1992).

Fischer, "Die chirurgishe Behandlung der Varizen Grundlagen and heutiger Stand: Surgery of Varicose Veins", Scheweiz, Rundshau Med, (PRAXIS), vol. 79, No. 7 (1990).
Devambez et al., "Self-Retaining retractor for surgery of varices", Phlebologie, vol. 41, No. 2, pp. 297-299 (1988).
*Endoscopy* [vol. 22, No. 4, 1990]: Document in German language 1990.
Vandamme, Jean-Pierre and Bonte, Jan, Vascular Anatomy in Abdominal Surgery, Thieme Medical Publishers, Inc. New York (1990).
Swobodnik, Atlas of Ultrasound Anatomy, Thieme Medical Publishers, Inc., New York (1991).
Respondent Terumo Cardiovascular Systems Corporation's Supplemental Responses to Maquet Cardiovascular L.L.C.'s Interrogatory Nos. 29, 32-33, 45-46, 51-62, 64 and 78 [redacted version with attached claim charts] Aug. 15, 2008.
Terumo's Proposed Claim Construction Oct. 31, 2008.
Maquet's Proposed Claim Constructions Oct. 31, 2008.
Maquet's Proposed Claim Constructions with Supporting Authority Nov. 19, 2008.
Public Complaint of Maquet Cardiovascular L.L.C. Under Section 337 of the Tariff Act of 1930 as Amended w/all exhibits Apr. 1, 2008.
Public Response of Respondents Terumo Corporation and Terumo Cardiovascular Systems Corporation to the Complaint and Notice of Investigation Jun. 9, 2008.
Public Amended Response of Respondents Terumo Corporation and Terumo Cardiovascular Systems Corporation to the Complaint and Notice of Investigation Oct. 27, 2008.
Respondent Terumo Cardiovascular Systems Corporation's Responses to Maquet Cardiovascular LLC's Seventh Set of Interrogatories (Nos. 91-95) Aug. 15, 2008.
Respondent Terumo Cardiovascular Systems Corporation's I Responses to Maquet Cardiovascular LLC's Third Set of Interrogatories [No. 78] Jun. 30, 2008.
Respondent Terumo Corporation's Responses to Maquet Cardiovascular LLC's Third Set of Interrogatories (No. 78) Jun. 30, 2008.
Respondent Terumo Corporation's Responses to Maquet Cardiovascular LLC's Sixth Set of Interrogatories (Nos. 82-86) Aug. 15, 2008.
Berci, "Endoscopy", 1976, ISBN 0-8385-2216-5.
"Enter a new realm", 2007, by Boston Scientific Corp.
"Vasoview competitive advantage", 2007, by Boston Scientific Corp.
"VasoView HemoPro endoscopic vessel harvesting system", 2007, by Guidant.
Samuels et al., "In Situ Saphenous Vein Arterial Bypass: A Study of the Anatomy Pertinent to its Use in Situ as a Bypass Graft with a Description of a New Venous Valvulatome", The American Surgeon, vol. 34, No. 2, pp. 122-130 (Feb. 1986).
Classen et al., "The Impact of Endoscopy", Gastroenterological Endoscopy, pp. 23-26. 2002.
"Preceptor" http://dictionary.reference.com/browse/preceptor. 2010.
"A new sense of security in endoscopic ligation", Sugical Laparoscopy & Endoscopy. 1990.
"Laparoscopic Surgery . . . the Next Generation." Surgical Laparoscopy & Endoscopy. 1992.
"Cabot Laparoscopic Irrigation System: Dissect/Lase/Cut/Irrigate/Aspirate through a single puncture", Surgical Laparoscopy & Endoscopy. 1990.
"Laparoscopic Cholecystectomy: A Minimally Invasive Treatment for Gallbladder Disease", Surgical Laparoscopy & Endoscopy. 2009.
"The DaVinci Line", Surgical Laparoscopy & Endoscopy.(1992).
"Nanticoke Advanced Laparoscopic/Thoracoscopic Instruments for the next generation of endoscopic surgery", Cabot Medical. 1992.
"Minimally Invasive Surgery: Laparoscopic Cholecystectomy", Karl Storz Endoscopy. 1992.
Advertisement: "Our New Line of Weck Instruments Brings The Feel of Open Surgery to Endoscopy", Linvatect Weck Endoscopy. 1993.
"The DaVinci Line", DaVinci Medical. 1992.
"VirtuoSaph Endoscopic Vein Harvesting System MCVS550", Terumo (product description). 2005.
History of Endoscopy, http://laparosoopv.blogs.com/endoscopyhistory/table_of_contents/. 2005.
Order Granting/Denying Request for Reexamination from 90/004,301 Patent Application. Oct. 1, 1996.
File History of U.S. Patent No. Re. 36,043 issued on Jan. 12, 1999.
File History of U.S. Appl. No. 10/897,157, filed Jul. 24, 2004.
File History of U.S. Appl. No. 10/052,016 filed Jan. 16, 2002.
File History of U.S. Patent No. 7,326,178 issued on Feb. 5, 2008.
File History of U.S. Patent No. 5,993,384 issued on Nov. 19, 1999.
File History of U.S. Patent No. 5,895,353 issued on Apr. 20, 1999.
Decision to merge reexamination and reissue proceedings for U.S. Patent No. 5,373,840 (control No. 90/004,301). Jan. 17, 1999.
Initial Expert Report of Paul Mitiguy, Oct. 31, 2008.
Memorandum re VasoView Feedback, Aug. 29, 1996.
Memorandum re VasoView Continued Release Plan, Dec. 11, 1996.
VasoView 2 Thoughts by Scott C. Anderson, Oct. 10, 1996.
Excerpt from Frazier Lab Notebook No. 144, Jun. 9, 1997.
Excerpt from Frazier Lab Notebook No. 152, Jun. 9, 1997.
Orbital Dissection Cannula Product Specification, Jun. 7, 1997.
Attachment A PPAQ Approval, Design Review, Design Freeze, Apr. 15, 1997.
VasoView Oribital Dissector Dissection Cannula IFU, Mar. 14, 1997.
Senior Staff update, May 5, 1997.
Disengagement project Scope for Enhanced Orbital Dissector, Dec. 18, 1997.
Excerpt from Frazier Lab Notebook No. 144, Nov. 3, 1997.
Excerpt from Tachi Callas Lab notebook No. 152, Nov. 3, 1997.
Orbital Dissection Cannula Enhanced Version Product Specification, Nov. 4, 1997.
Attachment A PPAQ Approval, Design Review, Design Freeze, Sep. 15, 1997.
Attachment A, Nov. 4, 1997.
McCoy Lab Notebook No. 166, Sep. 5, 1997.
VasoView III Development Team Market Preference Data Sheet, Sep. 4, 1997.
VasoView Big Balloon & Handle Market Preference Data Sheet, Mar. 11, 1997.
Product Specification History Dissection Tools, Jun. 27, 1996.
Product Specification for VasoView Dissection Tools (Rev date Apr. 15, 1996).
Memo to file re Monthly Program Review Summaries, Jul. 9, 1996.
Memo to Total Heart Team regarding Notes from Assn of PA Annual meeting, Jan. 26, 1996.
Memo re FMEA Rationale for SVH Balloon Dissection Cannula, Jun. 24, 1996.
Memo regarding Design Review Path Freeze Criteria OMS-BDS, Jul. 1, 1996.
Product Specification VasoView Balloon Dissection System, Jun. 21, 1996.
VasoView Balloon Dissection System Design Validation Conclusions, Jul. 10, 1996.
VasoView Balloon Dissection System Market Preference Data Sheet, Jul. 2, 1996.
Email regarding Pig Lab Results, Aug. 4, 1995.
Summary of Clinical, Jul. 3, 1996.
VasoView Balloon Dissection System Market Preference Data Sheet, May 29, 1996.
Chin Letter to FDA regarding Pre-Market notification 510K for Tapered Tip Balloon Dissection Cannula, Jul. 17, 1995.
VasoView Balloon Dissection System Market Release Meeting, Jul. 11, 1996.
VVII Team Meeting, Dec. 4, 1996.
Jeffrey Wayne Baxter deposition transcript, Sep. 26, 2008.
Albert Chin deposition transcript, Sep. 10, 2008.
Edwin Hlavka deposition transcript, Sep. 8, 2008.
John Lunsford deposition transcript, Sep. 24, 2008.
Justin Williams deposition transcript, Oct. 8, 2008.
Eric Willis deposition transcript, Oct. 7,.2008.
Responses of Maquet Cardiovascular, L.L.C. to Respondents Terumo Corporation and Terumo Cardiovascular Systems Corporation's Second Set of Requests for Admission, Nov. 3, 2008.
Supplemental Responses of Maquet Cardiovascular, L.L.C. To Respondents Terumo Corporation and Terumo Cardiovascular Systems Corporation's Requests for Admission No. 8-56, Nov. 20, 2008.
Responses of Maquet Cardiovascular, L.L.C. to Respondents Terumo Corporation and Terumo Cardiovascular Systems Corporation's Third Set of Request for Admission, Nov. 24, 2008.

Responses of Maquet Cardiovascular L.L.C. to Certain Interrogatories from Respondents Terumo Corporation and Terumo Cardiovascular Systems Corporation's First Set of Interrogatories [No. 3, 5, 7, 12, 23, 45, 48, 49, 59, 62, and 69], May 23, 2008.

Responses of Maquet Cardiovascular L.L.C. to Respondents Terumo Corporation and Terumo Cardiovascular Systems Corporation's First Set of Interrogatories [No. 1-78], Jun. 6, 2008.

Supplemental Responses of Maquet Cardiovasular L.L.C. to Respondents Terumo Corporation and Terumo Cardiovascular Systems Corporation's Interrogatory No. [5, 6, 8, 14, 32, 33 & 67], Jul. 23, 2008.

Supplemental Responses of Maquet Cardiovascular L.L.C. to Respondents Terumo Corporation and Terumo Cardiovascular Systems Corporation's Interrogatory No. 21, Sep. 5, 2008.

Responses of Maquet Cardiovascular L.L.C. to Respondents Terumo Corporation and Terumo Cardiovascular Systems Corporation's Third Set of Interrogatories [No. 87-115], Aug. 6, 2008.

Responses of Maquet Cardiovascular L.L.C. to Respondents Terumo Corporation and Terumo Cardiovascular Systems Corporation's Fourth Set of Interrogatories [No. 116-148], Aug. 11, 2008.

Supplemental Responses of Maquet Cardiovascular L.L.C. to Respondents Terumo Corporation and Terumo Cardiovascular Systems Corporation's Fourth Set of Interrogatories, Sep. 12, 2008.

Second Supplemental Responses of Maquet Cardiovascular L.L.C. to Respondents Terumo Corporation and Terumo Cardiovascular Systems Corporation's Interrogatory No. 130, 131, 133, 134, 136 & 137, Oct. 21, 2008.

Supplemental Response of Maquet Cardiovascular L.L.C. to Respondents Terumo Corporation and Terumo Cardiovascular Systems Corporation's Interrogatory No. 146 & 148, Oct. 31, 2008.

Responses of Maquet Cardiovascular L.L.C. to Respondents Terumo Corporation and Terumo Cardiovascular Systems Corporation's Fifth Set of Interrogatories [No. 149-152], Sep. 5, 2008.

Responses of Maquet Cardiovascular L.L.C. To Respondents Terumo Corporation and Terumo Cardiovascular Systems Corporation's Sixth Set of Interrogatories [No. 153-155], Sep. 10, 2008.

Responses of Maquet Cardiovascular L.L.C. to Respondents Terumo Corporation and Terumo Cardiovascular Systems Corporation's Seventh Set of Interrogatories, Nov. 21, 2008.

Responses of Maquet Cardiovascular L.L.C. to Respondents Terumo Corporation and Terumo Cardiovascular Systems Corporation's Eighth Set of Interrogatories, Nov. 24, 2008.

* cited by examiner

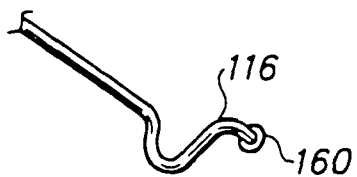
FIG. 9F
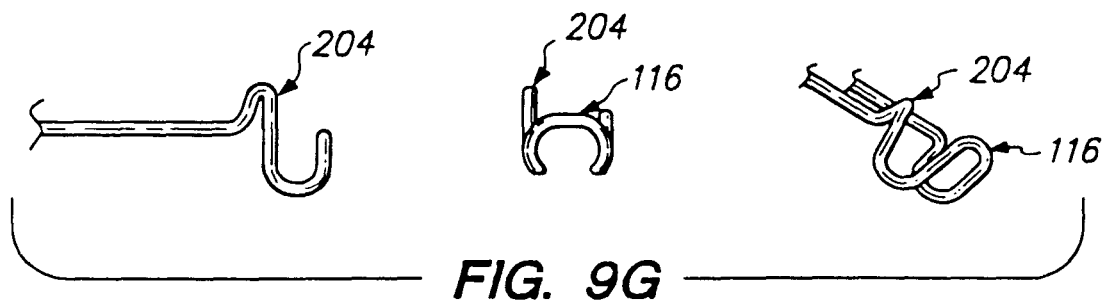
FIG. 9G
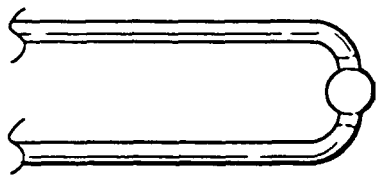 
FIG. 10A  FIG. 10B
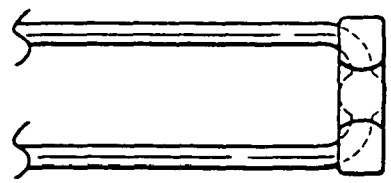 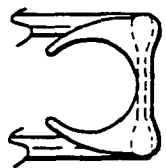
FIG. 10C  FIG. 10D

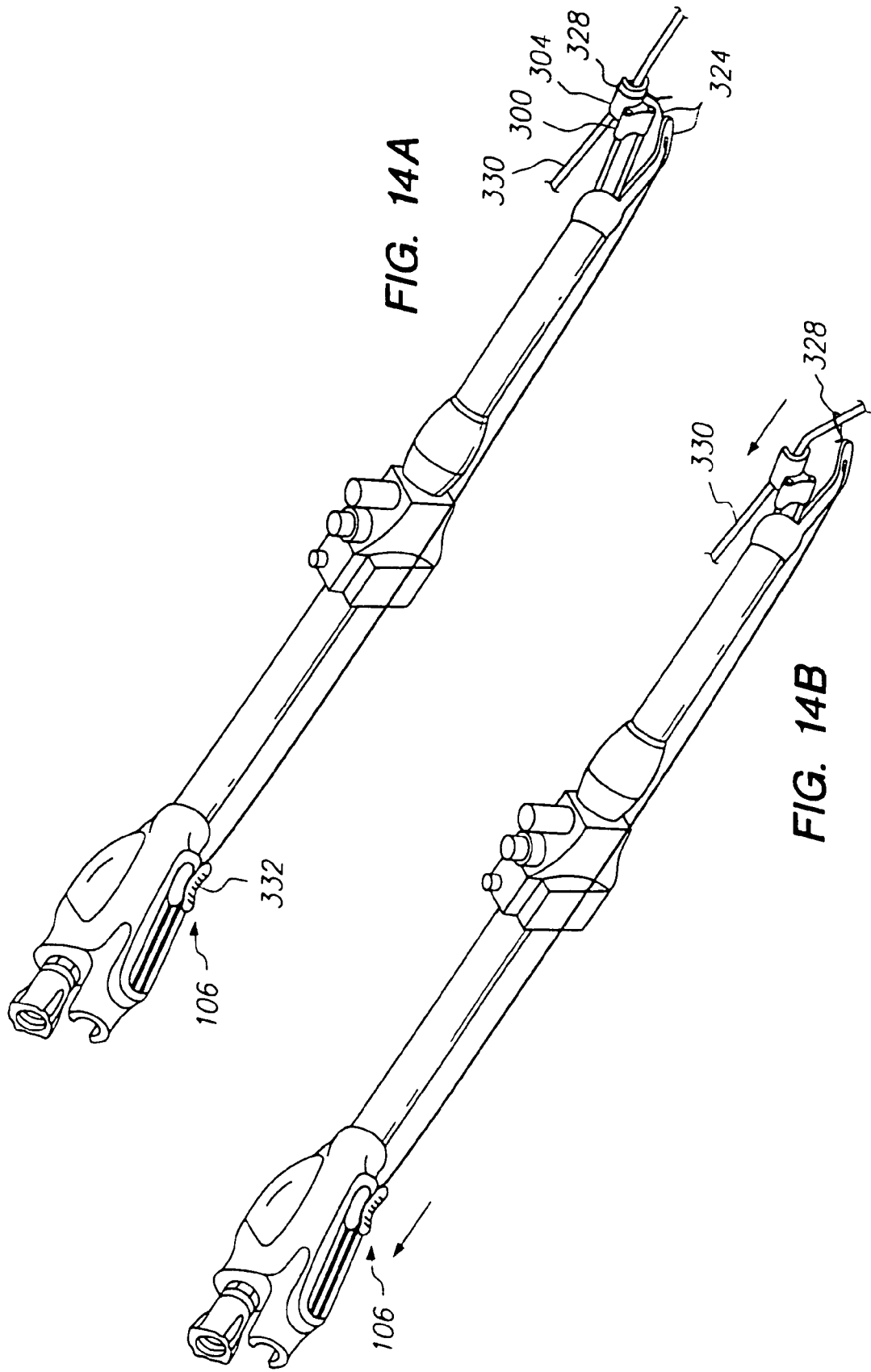

DEVICE AND METHOD FOR REMOTE VESSEL LIGATION

RELATED APPLICATIONS

This application is a continuation application of copending application Ser. No. 10/052,016 filed on Jan. 16, 2002 now U.S. Pat. No. 6,830,546, which is a continuation application of application Ser. No. 09/521,279, filed on Mar. 7, 2000, now U.S. Pat. No. 6,348,037, which is a continuation of application Ser. No. 09/200,218 filed on Nov. 25, 1998, now U.S. Pat. No. 6,162,173, which is a continuation-in-part application of application Ser. No. 09/102,723 filed on Jun. 22, 1998, now U.S. Pat. No. 5,895,353.

FIELD OF THE INVENTION

This invention relates to a cannula used for vessel retraction, and more particularly to a cannula and method that includes an endoscopic retractor for vessel ligation.

BACKGROUND OF THE INVENTION

Certain cannulas have surgical tools located within the cannula for performing surgical operations on a vessel of interest. The cannula is inserted into a surgical site with the distal end of the cannula positioned near the vessel of interest. An endoscope positioned within the cannula allows the surgeon to view the target area, and allows the surgeon to position the surgical tool correctly. One common procedure is to ligate a vessel or other tissue by tightening a suture loop tied as a slipknot on the vessel before transection to provide hemostasis to the vessel.

However, surgeons encounter several difficulties in ligation procedures. In one ligation procedure, a second incision must be made at the opposite end of the vessel of interest to ligate and transect the vessel. Multiple incisions are invasive and should be minimized if possible. In order to avoid this second incision, some conventional methods require tying a suture loop around the vessel, and pushing the loop along the vessel with a knot pusher until the opposite end is reached. Then, the loop is tightened to provide ligation. However, this procedure is difficult because the slipknot often catches on stumps of cut tributaries or other tissue, and then constricts around the vessel at the wrong position. Also, there is no easy method for transecting the vessel after the suture loop is tied to the vessel without potentially prematurely severing the suture.

Thus, a device and method is needed to allow remote, one-incision, ligation of a vessel which allows a suture loop to be moved reliably to the site of interest, and ensures that the transection instrument is able to transect the vessel, and cut the suture.

SUMMARY OF THE INVENTION

In accordance with the present invention, a retractor is positioned within a cannula with a dissection cradle end of the retractor positioned at the distal end of the cannula. The retractor includes a first portion that has an axis approximately parallel to a central axis of the cannula, and a second portion that has an axis which is at an angle with respect to the central axis of the cannula. The dissection cradle is located at the distal end of the second portion of the retractor. In another embodiment, the retractor includes two legs having substantially parallel axes that selectively protrude from the distal end of the cannula. The protruding legs support the dissection cradle formed in the shape of a loop that is positioned in a plane skewed relative to the axes of the legs, with a bottom of the loop directed away from the cannula. Thus, in operation, when the surgeon locates a vein and side branch of interest, the surgeon extends the retractor to cradle the vein in the dissection cradle. Once cradled, the retractor may be fully extended, pulling the vein away from the axis of the cannula, causing the side branch to be isolated and exposed to a surgical tool. The surgical tool may then be extended from within the cannula to operate on the isolated and exposed side branch.

In another embodiment, the top of the loop of the dissection cradle is flat and thin, allowing atraumatic support of the vein, and minimizing contact between the retractor and the surgical tool. In yet a further embodiment, the retractor includes a single leg with the loop formed by the one leg of the retractor, and with a stopper coupled to the distal end of the retractor. In still another embodiment, the cannula comprises a sliding tube which encases the retractor, and in a first position is extended out to encase the second portion of the retractor, and in a second position is extended to encase only the first portion of the retractor. In response to being in the first position, the second and first portions of the retractor are both approximately parallel to the axis of the cannula. In the second position, the second portion of the retractor is skewed relative to the axis of the cannula.

In accordance with an alternate embodiment of the present invention, a retractor is positioned within a cannula with a dissection cradle end of the retractor positioned at the distal end of the cannula. The dissection cradle comprises a shoulder part and a curved channel part. Suture forming a suture loop is threaded through a hole in a tension mount that is fixed to the distal end of the cannula and is abutted against the distal end of the shoulder. Upon advancement to the surgical site of interest, the suture loop is safely maintained in place due to the tension provided by the tension mount and the support provided by the shoulder. The curved channel provides a groove in which the vessel of interest may be cradled. Upon retraction of the retractor, the suture loop is displaced onto the vessel at the desired position for ligation. In one embodiment, the loop is tightened by detaching the proximal end of the suture from the cannula and pulling on the suture, constricting the suture loop. In an alternate embodiment, a manual controller for retracting the retractor is attached to the proximal end of the suture. Upon slidable retraction of the manual controller, the retractor is retracted, the loop is displaced onto the vessel, and the loop is tightened.

In a further embodiment, a transecting device is positioned within the cannula. The distal end of the tension mount is positioned to allow the distal end to be proximal to the shoulder of the dissection cradle responsive to the shoulder being in an axial position relative to the tension mount. This results in the suture and vessel being reliably positioned within reach of the transecting device for transection of the vessel and cutting of the suture.

Finally, in a preferred embodiment, the retractor has a distal end having an axis skewed relative to the central axis of the cannula, thus facilitating accurate positioning of the vessel and suture for transection and cutting, and ensuring the proper displacement of the suture loop onto the vessel in response to the retraction of the retractor.

BRIEF DESCRIPTION OF THE DRAWINGS

FIG. 7b is a side view of the retractor 112 of FIG. 7a.

FIG. 9f illustrates multiple views of a fifth alternate embodiment of cradle 116.

FIG. 9g illustrates multiple views of an embodiment of cradle 116 having a spur.

FIG. 10a illustrates a top view of an embodiment of the cradle 116 of FIG. 9c without a "C" ring.

FIG. 10b illustrates a side view of the cradle 116 of FIG. 10a.

FIG. 10c illustrates a top view of the cradle 116 of FIG. 9c with the "C" ring attached.

FIG. 10d illustrates a side view of the cradle 116 of FIG. 10c.

FIG. 14a illustrates a perspective side view of cannula 100 with retractor 112 extended.

FIG. 14b illustrates a perspective side view of cannula 100 with retractor 112 retracted.

DETAILED DESCRIPTION OF THE PREFERRED EMBODIMENTS

Figure 1:
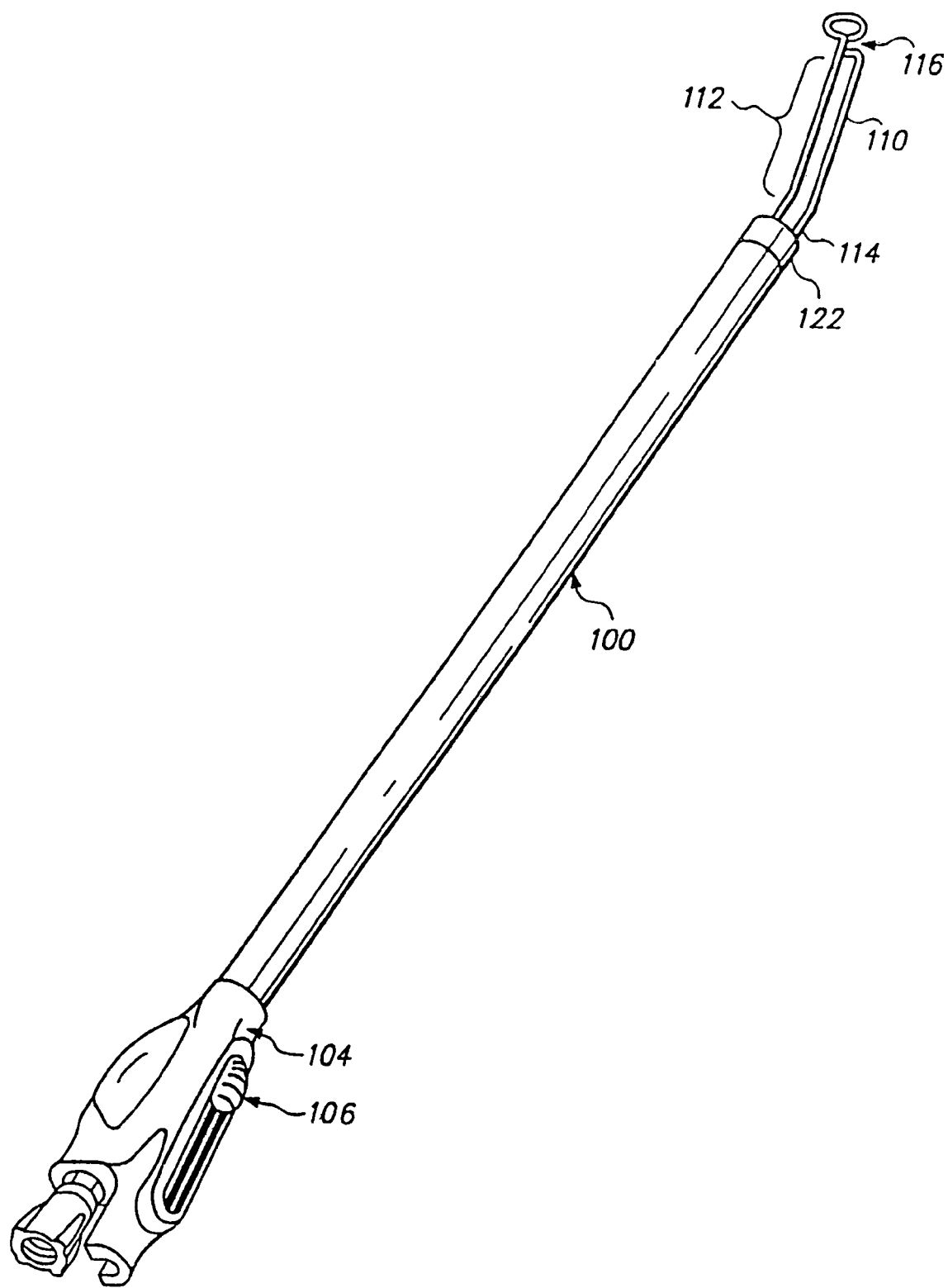
FIG. 1 is a perspective view of a preferred embodiment of cannula 100 showing retractor 112 in an extended position.

FIG. 1 illustrates a perspective view of a preferred embodiment of cannula 100 showing retractor 112 in an extended position. Cannula 100 includes an outer housing 102 of bioinert material such as polymed UD that may be approximately 12" to 18" in length. The proximal end of the cannula 100 is disposed in handle 104 that includes a button 106 which is coupled to retractor 112 for controlling the translational movement of retractor 112, as described in more detail below.

Figure 2A:
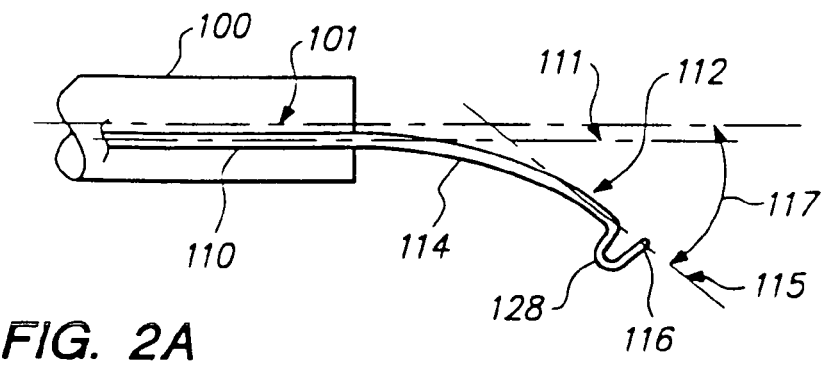
FIG. 2a is a cut-away side view of retractor 112 and cannula 100.

The distal end of the cannula houses a retractor 112, and optionally an endoscope 126 and a surgical tool 120, described below. FIG. 2a illustrates the retractor 112 in more detail. In one embodiment, retractor 112 is formed of resilient wire which has a smooth bend intermediate to a first portion 110 and a second portion 114 of the retractor. The retractor 112 is described as having two portions for ease of description, although the retractor 112 may be formed as an integrated structure. However, retractor 112 may also be manufactured from two separate portions 110, 114 that are coupled together. The first portion 110 of the retractor 112 is positioned within the cannula 100 with the axis 111 of the first portion 110 approximately parallel to the axis 101 of the cannula 100. The second portion 114 is positioned to bend away from the central axis 101 of the cannula. The angle 117 of displacement between the axis 115 of the second portion and the central axis 101 of cannula 100 may be any angle from zero to 180 degrees. The second portion 114 includes a dissection cradle 116 at the distal end of the second portion 114. The retractor 112 may be formed of bioinert material such as stainless steel, or a polymer such as nylon or polyetherimide, or other appropriately strong and springy plastic. In one embodiment, the retractor 112 includes a coating for lubrication, insulation, and low visual glare using, for example, parylene or nylon 11.

Figure 2B:
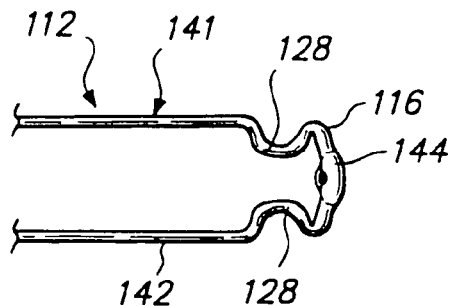
FIG. 2b is a top view of retractor 112.

FIG. 2b illustrates the retractor 112 formed with two legs. The legs 141, 142 of the retractor 112 at the distal end form the dissection cradle 116 in a loop or "U" shape, as shown in FIG. 2a. The top portion 144 of the U-shaped bend is preferably flattened to provide additional surface area for atraumatically supporting a vein 118 or vessel of interest. The side arches 128 of the dissection cradle 116 are used for skeletonizing or dissecting the vein from the surrounding tissues, as well as acting as walls to keep the vessel captured within the arch. The several embodiments of dissection cradle 116 are described in more detail below.

Figure 3A:
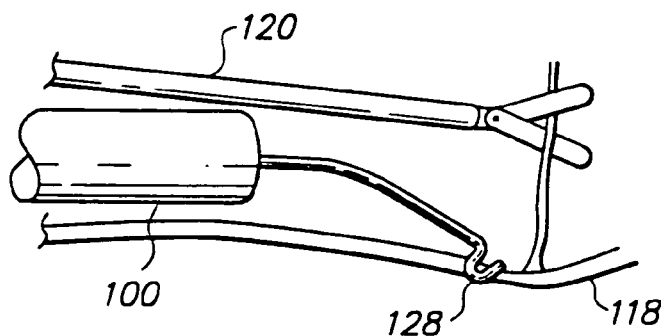
FIG. 3a is a perspective side view of cannula 100 with a saphenous vein positioned within the cradle 116.

FIG. 3a illustrates a perspective view of the cannula 100 in accordance with the present invention with the retractor fully extended, holding a saphenous vein 118; and also illustrates an external surgical tool 120 disposed adjacent the cannula 100 for performing a surgical operation, for example, severing a tributary or side branch of the vein 118. The vein is positioned within the side arches 128 of the cradle 116. The dissection cradle 116 may be used to cradle a vein, vessel, tissue or organ of interest, and surgical tool 120 may be any surgical tool suitable for performing a surgical procedure near the dissection cradle 116.

Figure 3B:
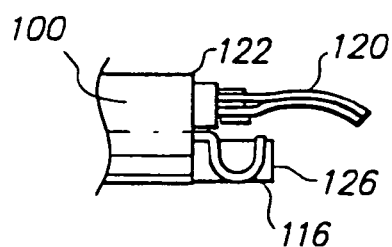
FIG. 3b is a perspective side view of the distal end 122 of cannula 100 in an embodiment in which an endoscope 126 and a surgical tool 120 are present and partially extended.
Figure 3C:
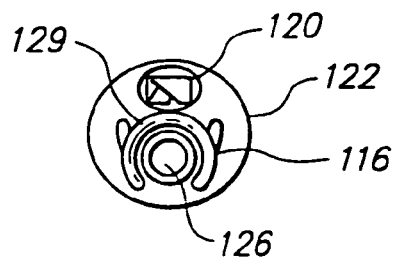
FIG. 3c is a front view of the distal end 122 of cannula 100 in which the surgical tool 120 and the retractor 116 are partially extended, and an endoscope 126 is present.

FIG. 3b illustrates a perspective view of cannula 100 in an embodiment in which the surgical tool 120 is positioned within the cannula 100, and an endoscope 126 is present. In this embodiment, cradle 116 preferably overlays the endoscope 126 with sufficient clearance to facilitate relative movements thereof. However, the endoscope may also be located adjacent the surgical tool 120. In one embodiment, endoscope 126 is positioned with cannula 100 to allow a clear field of view upon extension of the retractor 112. Surgical tool 120 is illustrated as scissors, used to sever a tributary or side branch of a saphenous vein 118. In this embodiment, surgical tool 120 is maximally displaced from the cradle 116 at the cannula end 122. More specifically, as shown in FIG. 3c, the "U"-shaped loop 129 of the cradle 116 is closest to the surgical tool 120. This ensures that a vein 118 or other tissue of interest is retracted away from the surgical tool 120 to facilitate manipulating the surgical tool 120 relative to the side branch or other tissue.

Figure 4A:
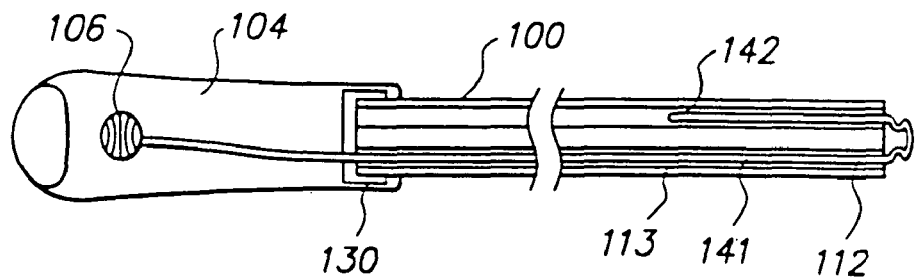
FIG. 4a is a cut-away top view of cannula 100.
Figure 4B:
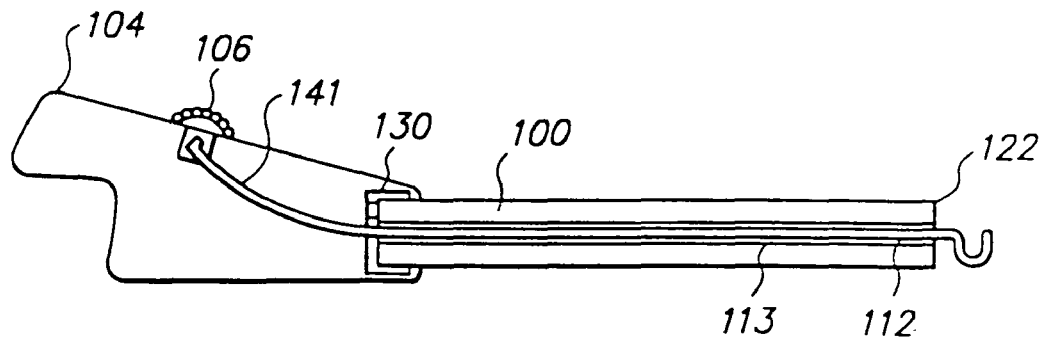
FIG. 4b is a cut-away side view of cannula 100.

FIG. 4a is a cut-away top view of cannula 100. The retractor 112 is slidably positioned within minor lumens 113 along the length of the cannula 100 within close tolerances in order to position the retractor 112 stably within the cannula 100. For example, in one embodiment retractor legs 141, 142 are approximately 0.045 inches in diameter and the lumens 113 encasing the legs 141, 142 are approximately 0.080 inches in diameter, as friction between the legs of the retractor 112 and the lumens 113 holds the retractor stably within the cannula. This configuration restricts rotational movement of the retractor to provide more stable retraction as compared with conventional retractors. The legs 141, 142 of the retractor 112 are formed of flexible, resilient material and are retained within the lumen 113 in substantially straight or flat orientation, but may return to a material bend or curve, as illustrated in FIG. 5a, as the retractor 112 is extended from the distal end of the cannula 100.

The leg 141 of the retractor 112 passes through a sliding gas or fluid seal 130 at the proximal end of the lumen 113. The leg 141 of the retractor 112 passes out of the cannula 100 and into handle 104 for attachment to a slider button 106 for facilitating translational movement of the retractor 112 from the proximal or handle end of the cannula 100. However, other types of control devices such as knobs, grips, finger pads, and the like may be linked in conventional ways to the retractor 112 in order to manually control the translational movement of retractor 112. In one configuration, the proximal end of leg 141 is bent relative to the axis of the cannula, and the button 106 is attached to the bent position of the leg 141 to facilitate moving the button 106 and the retractor 112 translationally under manual control. The button 106 preferably includes lateral grooves to prevent finger or thumb slippage during sliding manipulation of the retractor 112.

Thus, in the operation of a preferred embodiment, a user actuates the slider button 106 to extend retractor 112 out of the lumen 113 at the distal end of the cannula 100. In one embodiment, the resilient retractor 112 is formed in a smooth bend, as shown in FIG. 2a, and gradually deflects away from the central axis 101 of the cannula 100 as the retractor is extended. Upon encountering the target vessel or tissue of interest, the vessel is restrained in the cradle 116, and a lateral resilient force is exerted on the target vessel in a direction away from the cannula. The vessel is thus pushed away from the axis of the cannula 100, isolating it from surrounding tissue or adjacent vessels such as tributaries or side branches. As a tributary is thus isolated, a surgical tool 120 such as cauterizing scissors may be safely employed to operate on the tributary without harming the saphenous vein 118. When retracted into the cannula 100, the retractor 112 is again resiliently straightened or flattened.

Figure 5A:
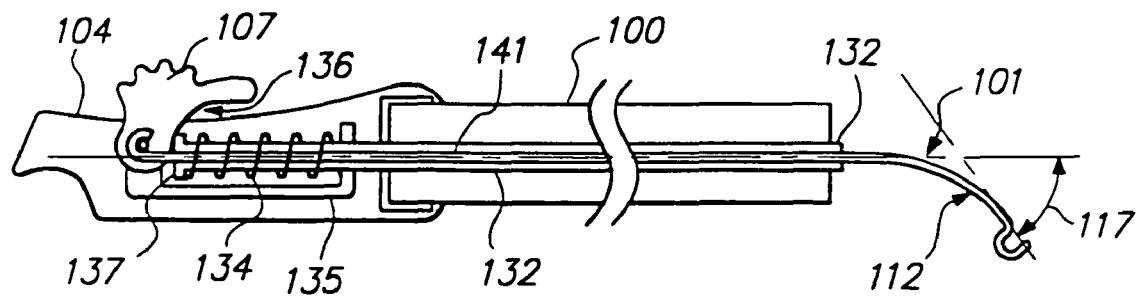
FIG. 5a is a cut-away view of a sliding tube embodiment of cannula 100 in a first position.
Figure 5B:
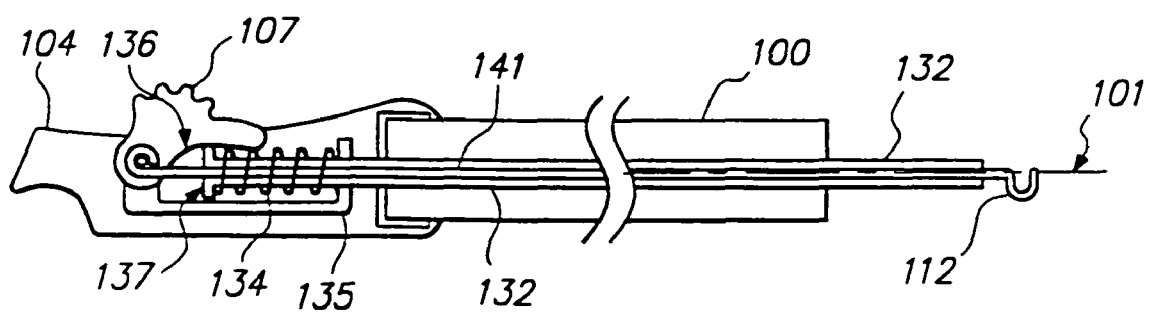
FIG. 5b is a cut-away view of the sliding tube embodiment of FIG. 5a in a second position.

In an alternate embodiment as illustrated in FIGS. 5a and 5b, a sliding tube 132 is added to provide operational versatility to cannula 100. In a first position, the sliding tube 132 is retracted and the retractor 112 protrudes from the distal end at an angle with respect to the central axis 101 of the cannula 100. In a second position, the sliding tube 132 is extended out, temporarily straightening the retractor 112. As illustrated in FIG. 5a, a sliding tube 132, in a first position encases the retractor 112 up to the point at which the retractor 112 curves away from the central axis 101 of the cannula thus allowing the retractor 112 to displace and isolate a target vessel. The proximal end of the sliding tube 132 is linked to button 107 for translationally moving retractor 112 as well as actuating the sliding tube 132. In one embodiment, as illustrated in FIG. 5a, the sliding tube 132 is in a first position with the button 107 in an upright position. A spring 134 is coupled between a support structure 135 and the proximal end 137 of the sliding tube 132. In the first position of sliding tube 132, the spring 134 is extended fully and exerts little or no force on the sliding tube 132. Of course, sliding tube 132 may be manually manipulated without linkage to a button 107.

To extend the sliding tube 100, button 107 is pushed down. As illustrated in FIG. 5b, the button 107 has a cam surface 136 which pushes on the proximal end 137 of the sliding tube 132 as the button 107 is pressed. The sliding tube 132 is pushed forward, overcoming the resilient force of spring 134, to encase the retractor 112 and decrease angle 117 between the distal end of the retractor 112 and the central axis 101 of the cannula 100. Upon releasing the button 107, the spring force urges the proximal end 137 of the sliding tube 132 back toward the first position against button 107. The sliding tube 132 is formed of material having sufficient strength to force the retractor 112 to straighten out the angle 117, and the retractor 112 is formed of resilient material having a sufficient flexibility to straighten out the angle 117 in response to a tube 132 being slid over the retractor 112, but having sufficient rigidity to cradle and dissect a target vessel. Resiliency of the retractor 112 ensures return to the downwardly-curved shape after being released from tube 132. Thus, in accordance with this embodiment, a user may employ the curved retractor for certain applications and employ the straightened form for other applications. A manual actuator may be configured in other ways than button 107 to extend the sliding tube 132 in response, for example, to being pulled up instead of pushed down.

Figure 6A:
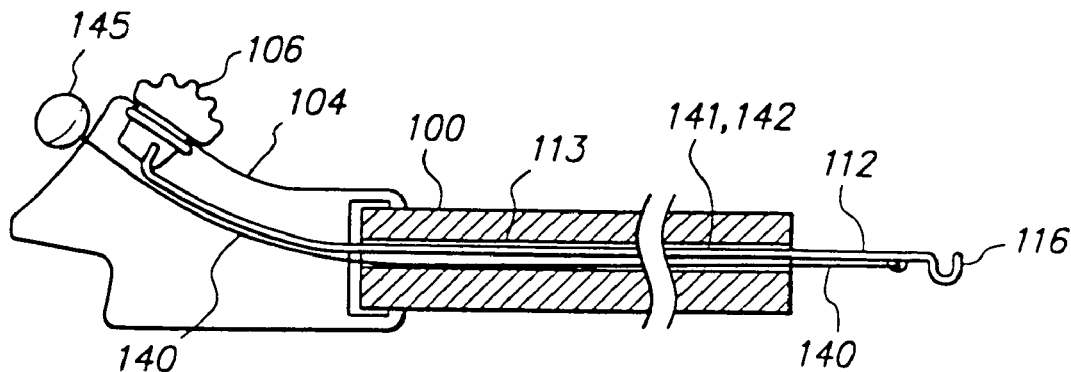
FIG. 6a is a cut-away view of an embodiment of cannula 100 having an angling device 140.
Figure 6B:
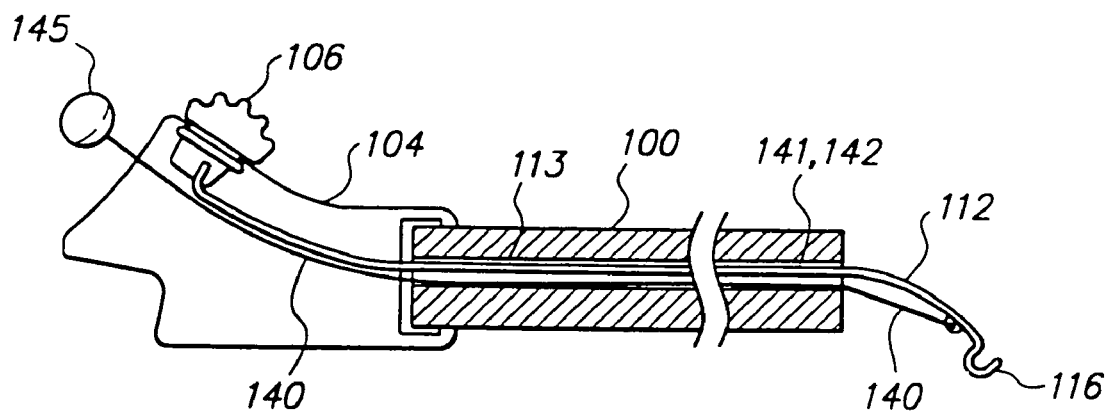
FIG. 6b is a cut-away side view of the apparatus illustrated in FIG. 6a in which the retractor 112 is extended and the angling device 140 is actuated.

Another embodiment employs a retractor 112 which has a naturally straight shape. As illustrated in FIGS. 6a and 6b, an angling device 140 is disposed between the distal end of the retractor 112 and the proximal end of the cannula. The angling device 140 may be positioned within the same lumens 113 as the retractor 112 and preferably may comprise two wires coupled to points below the cradle 116 of the retractor 112 substantially in parallel positions on each of the legs 141, 142.

Figure 6C:
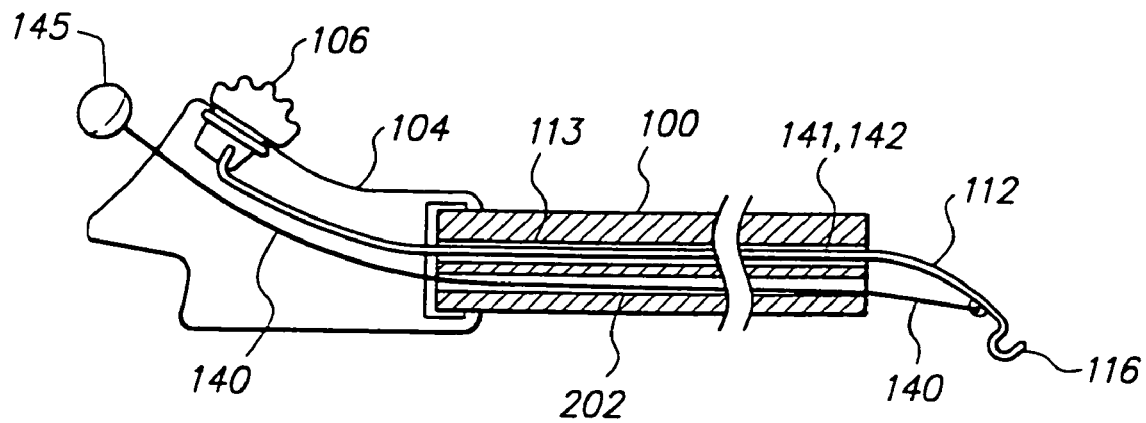
FIG. 6c is a cut-away side view of the angling device embodiment in which the angling device 140 is in a separate lumen from the retractor 112.

Upon extending the retractor 112 using button 106, the angling device 140 is extended with the retractor 112. The angling device 140 is coupled to a handle 145 at the proximal end of the cannula 100 to facilitate establishing an angle in the retractor 112 by pulling with a backward force on the angling device 140. As illustrated in FIG. 6b, after the retractor 112 is extended, the angling device 140 is actuated and a bend is created in the retractor 112 as the backward force exerted on the distal end of the retractor is exerted against the relatively fixed position of the retractor legs 141, 142 disposed within the lumens 113. As shown in FIG. 6c, the angling device 140 may also be located in a separate lumen 202 from the retractor 112 with part of the angling device 140 positioned outside of the cannula 100 when the retractor 112 is in the retracted position.

Figure 7A:
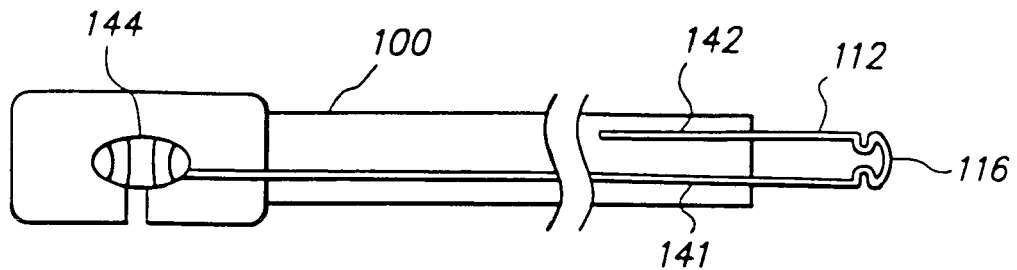
FIG. 7a is a cut-away side view of a twistable retractor 112 in a straight position.
Figure 7C:
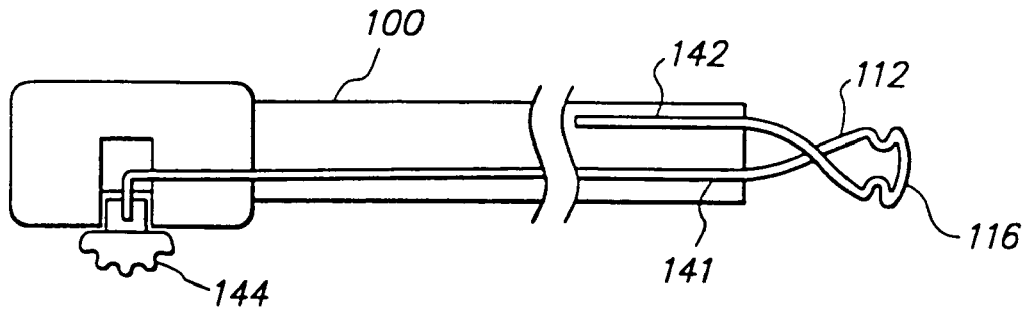
FIG. 7c is a cut-away side view of twistable retractor 112 in a crossed position.
Figure 7B:
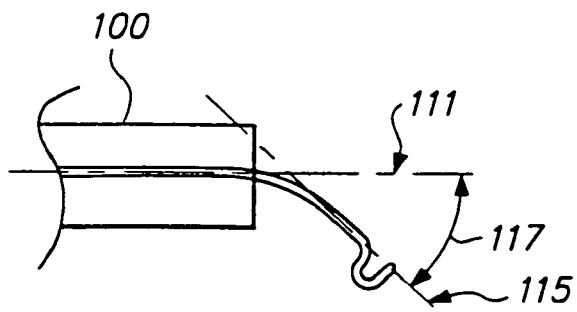
Figure 7D:
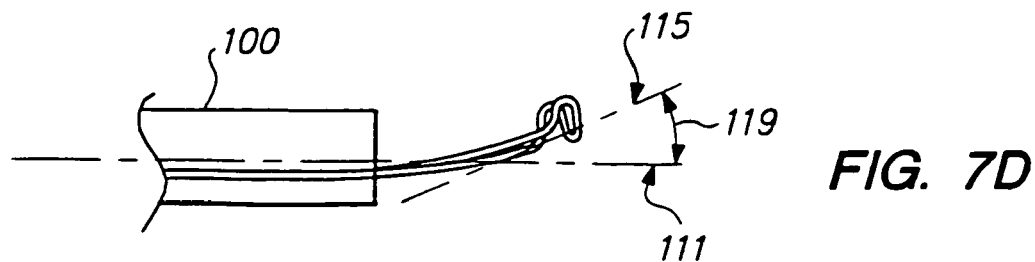
FIG. 7d is a side view of the retractor 112 of FIG. 7c.

FIG. 7a illustrates another embodiment of cannula 100 in which the retractor 112 is pre-formed with one leg 141 of the retractor 112 bent at an angle at its proximal end skewed to the axis of the distal end of the other leg 142. The bent portion of the leg 141 may be linked to a sliding knob 147 for convenient manual manipulation of this embodiment of the invention. Upon sliding the knob 147, the leg 142 coupled to knob 147 is twisted rotationally. The two legs 141, 142 of retractor 112 are coupled together via cradle 116. The axis of the second portion of the retractor 112 in the first position is at a first angle 117 to the axis of the cannula 100, as shown in FIG. 7b. As knob 147 is moved, leg 141 is rotated and crosses under leg 142, as shown in FIG. 7c. This causes cradle 116 to flip 180 degrees and bends the retractor 112 at a second angle 119, as shown in FIG. 7d. Thus, if a vessel is disposed on one side of cradle 116 or cannula 100 while the retractor 1'12 is in the first position, then upon rotating the knob 147, the vessel is transported to the other side of the cannula 100. This allows the user to isolate the vessel by simply actuating knob 147.

Figure 8A:
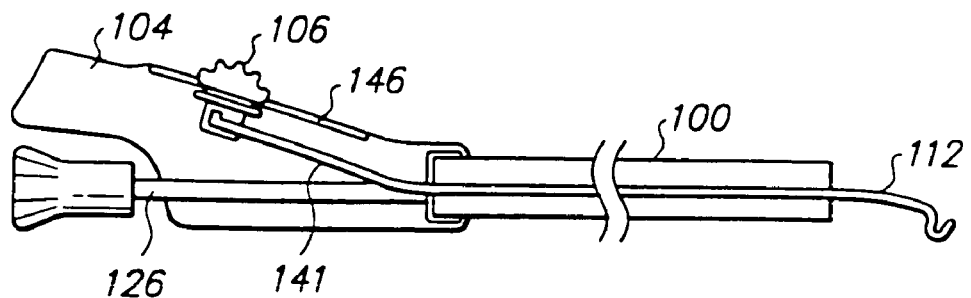
FIG. 8a is a cut-away side view of the handle 104.
Figure 8B:
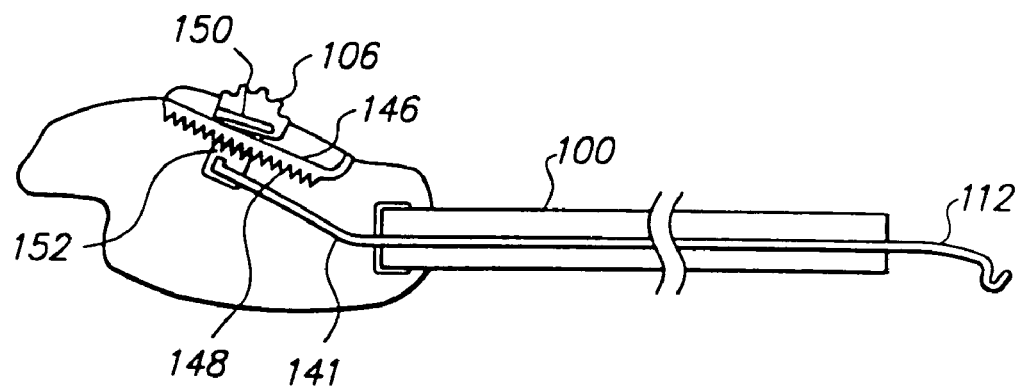
FIG. 8b is a cut-away side view of an alternate embodiment of handle 104.

FIG. 8a illustrates a cut-away side view of button 106 on the handle 104 of cannula 100, with an endoscope 126 positioned within cannula 100. As mentioned above, button 106 is coupled to one leg 141 of the proximal end of retractor 112. Sliding the button 106 in groove 146 translationally moves the retractor 112. Groove 146 is preferably minimally wider than the shaft of button 106 to minimize excessive horizontal movement of button 106 while still allowing smooth translational movement of button 106. As illustrated in FIG. 8b, the button 106 may include locking or ratcheting teeth 152 to give tactile feedback of its location, and to positively retain the button and the associated leg 141 in an extended or retracted position. Several mating teeth 148 are located underneath groove 146, and a spring member 150 is attached to button 106 to exert pressure against the base of groove 146, to engage mating teeth 148, 152. When a force is applied on the top of button 106, the interlocking sets of teeth are disengaged and button 106 can move freely. Upon achieving the desired extension or retraction of the leg 141, button 106 is released and is retained place by the engaged teeth 148, 152.

Figure 9A:
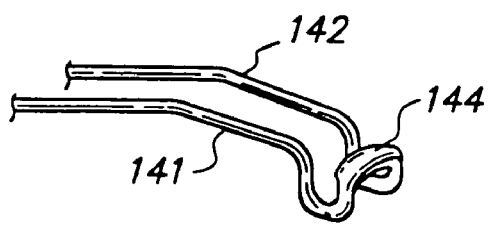
FIG. 9a is a side view of cradle 116.

FIG. 9a illustrates a top view of cradle 116 in an embodiment in which the cradle 116 is formed by two legs 141, 142 of retractor 112. The distal end of the legs form "U"-shaped side guides. The top 144 of the distal portion of the "U" is preferably flattened. This provides atraumatic support for the target vessel retained within cradle 116. Additionally, by minimizing the thickness of distal portion 144, contact with other devices in close proximity with retractor 112 is minimized.

Figure 9B:
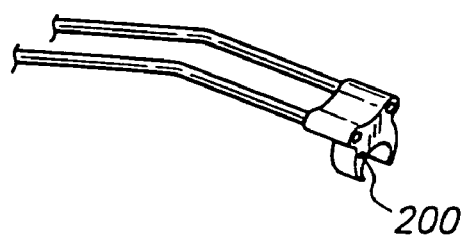
FIG. 9b illustrates a first alternate embodiment of cradle 116.

The cradle 116 may have other effective shapes, for example, as illustrated in FIG. 9b in which a "C" ring element is attached to legs of the cradle 116. The "C" ring may have a small hole 200 in one side with an axis approximately parallel to the axis of the retractor 112. This hole 200 is used to hold suture or other ligating materials, and may also be used as a knot pusher. As shown in FIGS. 10a and 10b, in an alternate embodiment of the embodiment of FIG. 9b, the retractor 112 is formed and flattened and a "C"-shaped ring is coupled to the retractor 112 by, for example, gluing or molding the "C" ring to the distal end of the retractor 112, as shown in FIGS. 10c and 10d.

Figure 9C:
FIG. 9c illustrates multiple views of a second alternate embodiment of cradle 116.
Figure 9D:
FIG. 9d illustrates multiple views of a third alternate embodiment of cradle 116.
Figure 9E:
FIG. 9e illustrates multiple views of a fourth alternate embodiment of cradle 116.

Referring back to FIGS. 9c, 9d, and 9e, the side guides of the cradle may include a loop 129 in a "V" shape, an arced "U" shape, or a semi-circular shape. In one embodiment, as illustrated in FIG. 9f, the retractor 112 has only one leg 141, and the cradle 116 is formed by the leg 141. A stopper 160 is coupled to the end of the leg 141 to serve as a guide to retain the target vessel, and add a blunt surface to the end of the wire, for example, for pushing and probing tissue. FIG. 9g illustrates a retractor 112 having a spur 204 formed in one or both legs 141, 142 for allowing the retractor 112 to be used for dissection. Sinusoidal, half-sinusoidal, and other geometric configurations may be used equally effectively as the shape of loop 129 in accordance with the present invention.

Figure 11:
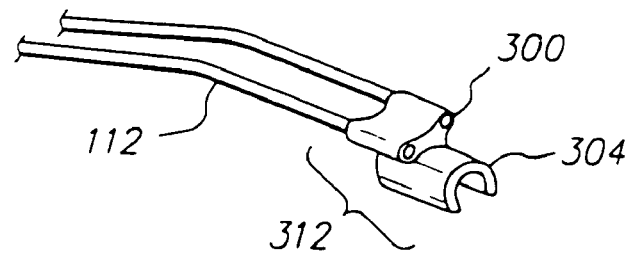
FIG. 11 illustrates a perspective side view of cradle 312 for remotely ligating vessel.

FIG. 11 illustrates an alternate dissection cradle 312 for use in remote vessel ligation. Remote vessel ligation as discussed above is necessary to provide hemostasis to a vessel or other tissue after the vessel has been transected. In accordance with the present invention, hemostasis is accomplished by tightening suture formed in a loop adjacent the point of transection of the vessel. However, it is preferable to provide hemostasis to the vessel without incising the body a second time at the point of transection. The cannula 100 and dissection cradle 312 provide this functionality.

Figure 12:
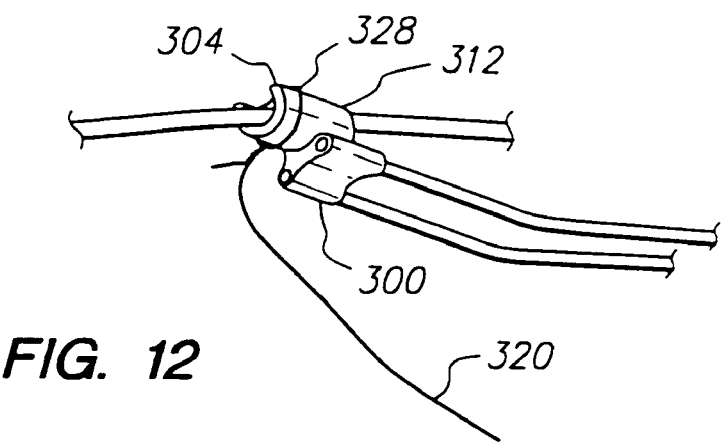
FIG. 12 illustrates a perspective side view of cradle 312 in operation.

At the distal end of the retractor 312, a shoulder part 300 is preferably formed of a rigid plastic encapsulating the distal end of the retractor 112. A curved channel part 304 is attached to the shoulder 300. The curved channel 304 is formed in the shape of a "C" as shown. The curve of curved channel 304 exposes a portion of the distal face of the shoulder 300, upon which a suture loop 328 may be abutted, as shown in FIG. 12. Other shapes, such as those shown in FIG. 9a-e, may also be used as curved channel 304.

FIG. 12 illustrates the manner in which the suture loop 328 is transported safely to the point of transection. The loop 328 is formed as a slipknot, which may be cinched tighter by exerting a backwards force on the free end of the suture 320. The suture loop 328 is tied around the vessel and the curved channel part 312, and is abutted against the shoulder 300. Next, the loop 328 is tightened onto the curved channel 304 by pulling back on the free or proximal end of the suture 320. The loop 328 is tightened sufficiently to permit safe advancement, but is provided with sufficient slack to allow displacement of the loop 328 onto the vessel adjacent the point of transection upon retraction of the retractor 312 into the cannula 100.

Figure 13:
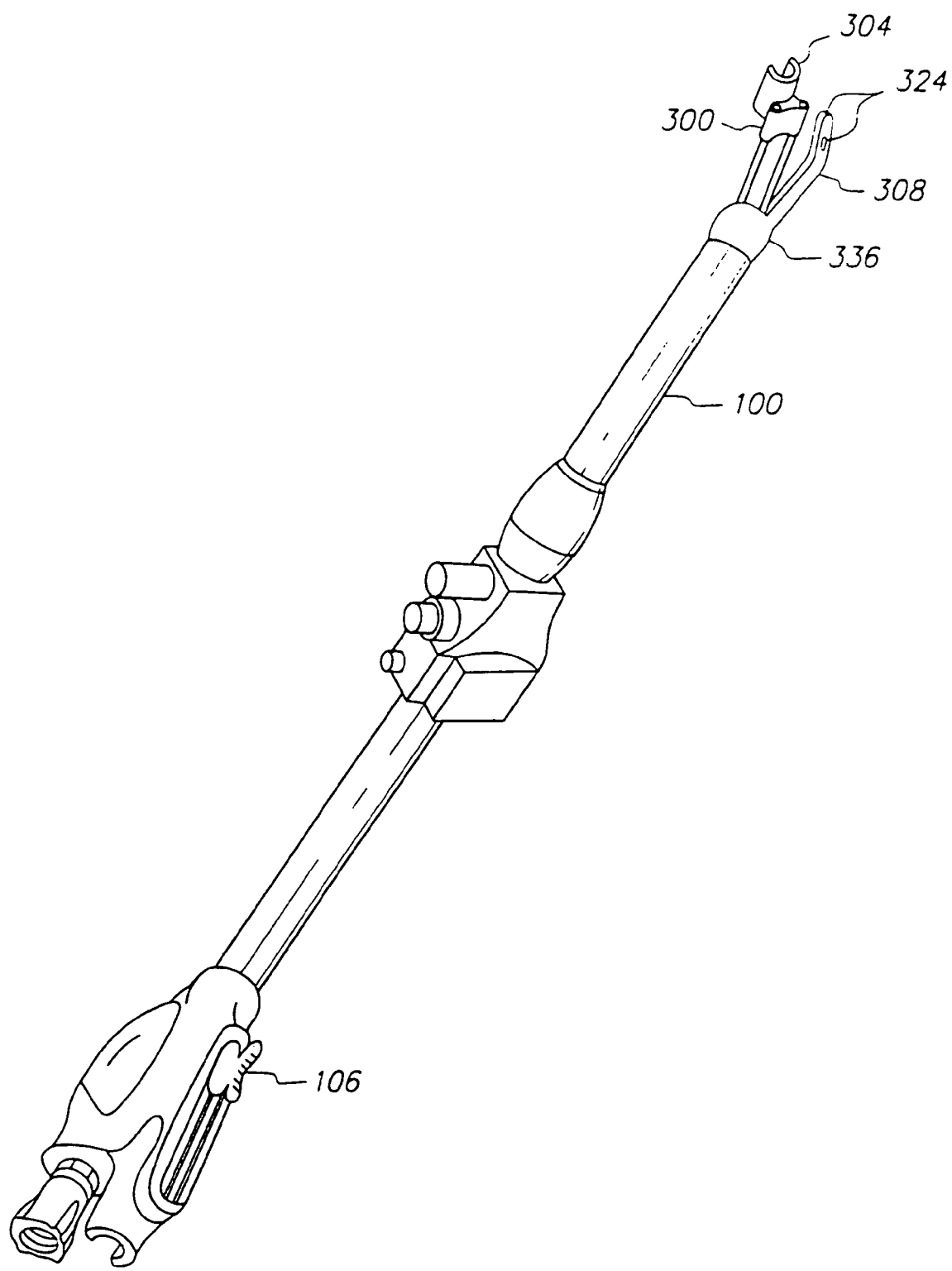
FIG. 13 illustrates a perspective side view of cannula 100 having a dissection cradle 312.

One embodiment of the present invention for exerting a backward or disengaging force on the loop 328 is shown in FIG. 13. FIG. 13 illustrates a tension mount 308 attached to cannula 100 for providing secure transport of the suture 320 to the surgical site of interest and for providing a controlling mechanism for tightening the suture loop 328 around the vessel when ligation is desired. The tension mount 308 is also formed of rigid plastic with some flexibility to allow other surgical tools 120 (not shown) to extend beyond the distal end of the tension mount 308, and to allow atraumatic advancement of the tension mount 308 through the body. The distal end of the tension mount 308 includes a hole 324 through which the suture is threaded to tighten the suture loop 328. The distal end of the tension mount 308 protrudes toward the central axis of the cannula 100. This ensures that the vessel and the suture will be in the optimal position for transection or cutting after the loop 328 has been displaced onto the vessel. Additionally, the forward angle of the tension mount 308 also ensures that the loop 328 will be displaced onto the vessel upon retraction of the retractor 312, as discussed in greater detail below. The length of the tension mount 308 is chosen to allow the cradled vein to remain in endoscopic view upon advancement. Alternatively, a long knot pusher may be used in place of tension mount 308. The suture 320 is looped around the vessel and the curved channel 304, previously described. However, the free end of the suture 320 is threaded through a hole in the long knot pusher disposed within the cannula 100. The cannula 100 and knot pusher are advanced to the point of transection. Displacement of the loop 328 occurs by advancing the knot pusher while maintaining the position of the dissection cradle 312 relative to the vessel. After the loop 328 is displaced onto the vessel, the loop 328 is tightened by pulling backward on the suture 320. The long knot pusher may contain a lumen which runs the length of the cannula 100 or it may contain a shorter lumen which starts at the tip of the cannula and exits a side of the cannula 100 after a short distance proximally.

FIG. 14a illustrates the operation of the cannula 100 which has a tension mount 308. The cradle 312 holds a vessel 330. The vessel 330 is safely cradled in the curved channel 304 as the cannula 100 is advanced. The suture 320 is threaded through the hole 324 disposed in the distal end of the tension mount 308. The distal end of the suture 320 is then formed into a suture loop 328 around the vessel 330, and is abutted against the shoulder 300. In this embodiment, the proximal end of the suture 320 is wrapped around a cleat 332 on button 106 at the proximal end of the cannula 100. The loop 328 is tightened around curved channel 304 by winding the proximal end of the suture 320 around the cleat 332 which has the effect of pulling on the suture loop 328 and cinching the knot tightly around the curved channel 304 against the shoulder 300. The suture loop 328 may now be safely advanced to the surgical site as excessive slack does not occur in the loop 328, which would cause the loop 328 to be dislodged from the cradle 302. In an alternate embodiment, the loop 328 is tightened responsive to the sliding of the button 106. The button 106 has a lock with a release mechanism which restricts the sliding of the button 106. When the loop 328 requires tightening after displacement onto the vessel, the kick is released and the button 106 is retracted. This embodiment ensures that the surgeon does not accidentally dislodge the loop 328 from the shoulder 300 by prematurely retracting the retractor 312 into the cannula 100.

Upon reaching the site of interest, the loop 328 is displaced onto the vessel 330 by sliding a manual controller backwards, causing the retractor 112 to retreat to an axial position. In the embodiment of FIGS. 14a and b, the loop 328 is displaced by sliding the button 106 backwards. Upon sliding the button 106 backwards, as shown in FIG. 14b, the cradle 312 is retracted into cannula 100, causing the loop 328 to be forcibly displaced from the shoulder 300 of the dissection cradle 312 onto the vein 330 at the desired location.

After displacement onto the vessel 330, a knot tightener 340 is then used to tighten the suture loop 328 onto the vessel 330 to provide hemostasis. In the embodiment of FIGS. 14a and b, the loop 328 is tightened onto the vessel 330 as the proximal end of the suture 320 is wound around the cleat 332. The proximal end of the suture 320 could also simply be detached from the proximal end of the cannula 100, and the loop 328 tightened by pulling on the free end of the suture 320. Alternatively, the loop 328 may be tightened by fixing the proximal end to the button 106. Sliding the button 106 towards the proximal end of the cannula 100 exerts a backwards force on the loop 328, tightening the loop 328.

Figure 15:
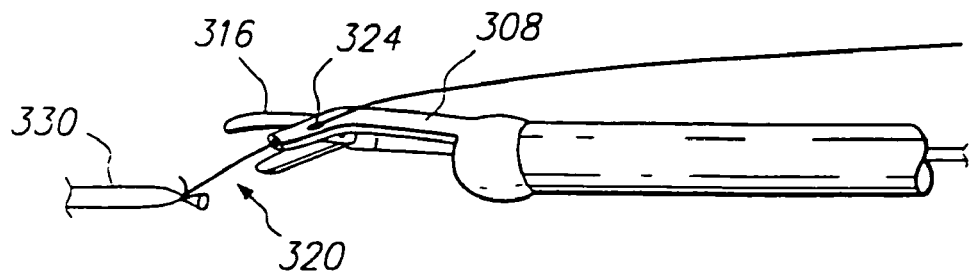
FIG. 15 illustrates a perspective side view of cannula 100 with transection device 316.

FIG. 15 illustrates the use of the transection instrument 316 in accordance with the present invention. The transection instrument 316 is preferably endoscopic shears disposed within cannula 100. The shears 316 are positioned between tension mount 308 and cradle 312. After the vessel 330 has been ligated as described above, the shears 316 are extended to transect the vessel. As the vessel is tied by the suture 320 which passes into the tension mount 308, the vessel is thus placed within easy reach of the blades of the shears 316. The tension mount 308 is formed with a slight bend toward the center of the cannula 100 to facilitate keeping the vessel 330 within the apex of the open blades of the shears 316. After transecting the vessel 330, the vessel 330 will fall away as shown in FIG. 15. The suture 320, however, is now within the apex of the open blades of the shears 316. The shears 316 are then extended again and used to cut the suture 320. The ligated vessel 330 remains in the surgical site, and the graft is able to be removed through the first and only incision.

Figure 16A:
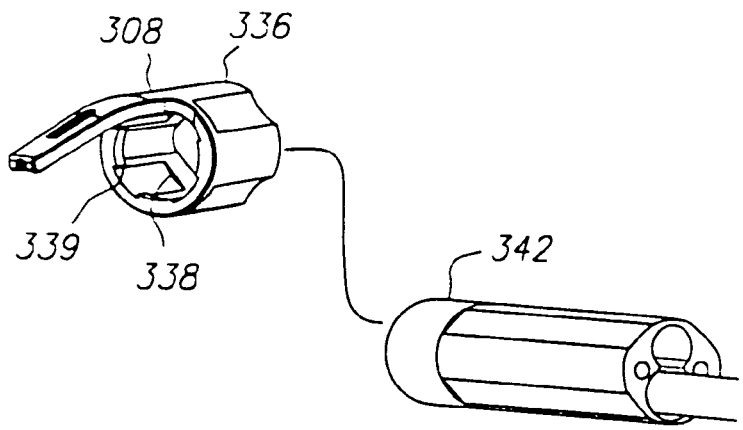
FIGS. 16 a-c illustrates multiple views of tension mount 308.
Figure 16B:
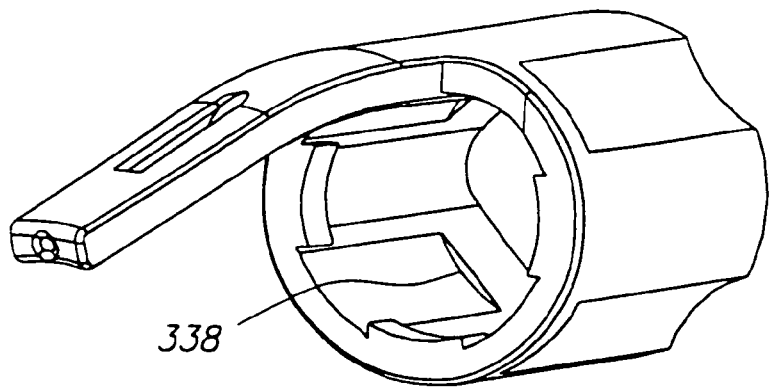
Figure 16C:
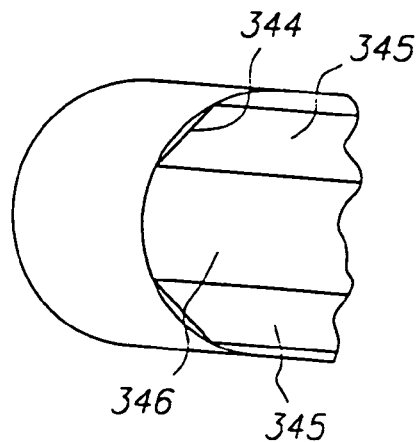

FIGS. 16a-c illustrates multiple views of tension mount 308. FIG. 16a illustrates tension mount 308 attached to a collar 336. The collar 336 allows the cannula 100 to be used without a tension mount 308 for the initial transection operation in which the tributaries of the vessel 330 are transected to allow the main length of the vessel to be extracted from the body. For this initial transection operation, the tension mount 308 may interfere with this procedure, and thus should be removed.

The collar 336 of the tension mount 308 has proximal and distal ridges 338, 339 disposed on its inner surface. FIG. 16b illustrates in greater detail the proximal ridge 338 which mates with ridges disposed on the cannula surface. As shown in FIG. 16c, the distal end 342 of the cannula 100 is smooth plastic or other bioinert material on which the ridged collar 336 may slide easily. Ridges 346 situated at flat or recessed portions 345 on the surface of the body of cannula 100 form edges 344 for retaining the collar 336. Upon sliding the collar 336 onto the distal end 342 of the cannula 100, the collar 336 resiliently expands and ridges 338, 339 of the collar 336 align with edges 344 of the cannula 100. Upon alignment, the collar 336 resiliently contracts and thus forms a secure fitting of collar 336 on cannula 100. When the surgeon wants to remove the collar 336, the surgeon simply twists the collar 336 to misalign the ridges 338, 339 of the collar with ridges 346 of the cannula 100, causing the collar 336 to resiliently expand again, thus allowing the collar 336 to be easily removed from the cannula 100.

Figure 17:
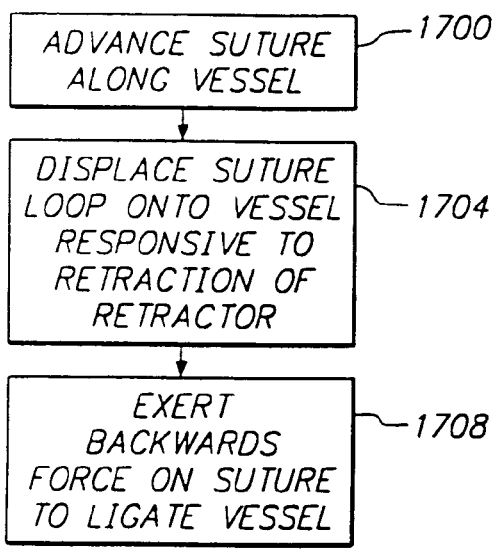
FIG. 17 is a flowchart illustrating the process of remote ligation of a vessel in accordance with the present invention.

FIG. 17 illustrates a method of performing remote vessel ligation in accordance with the present invention. The surgeon advances 1700 a suture loop 328 along a vessel to a remote site from incision. The suture loop 328 is displaced 1704 onto the vessel responsive to retraction of the retractor, and, responsive to exerting 1708 a backward force on the suture, the vessel is ligated.

Figure 18:
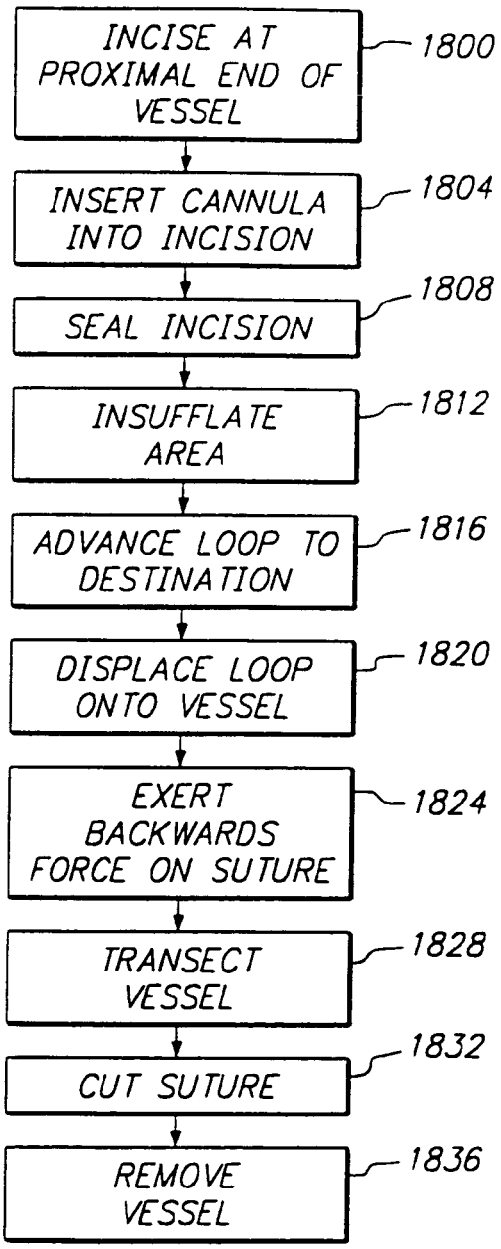
FIG. 18 is a flowchart illustrating the process of remote ligation and vessel harvestation under gas insufflation.

In a further embodiment, as shown in FIG. 18, the one-incision ligation and harvesting operation is performed under gas insufflation. First, an incision is made 1800 at the desired beginning point of the graft. For example, for saphenous vein harvesting for coronary artery bypass grafting, the incision is made at the knee. Next, the cannula 100 is inserted 1804 into the incision, and the incision is sealed 1808. A tunnel is formed along the vessel by insufflating 1812 the area with gas. The suture loop 328 is safely advanced 1816 to the destination. For saphenous vein harvesting, the loop 328 is advanced to its origin at the saphenofemeral junction. The loop 328 is displaced 1820 onto the vessel, and a backwards force is applied 1824 to the suture 320 to ligate the vessel. The vessel is transected 1828 and the suture is cut 1832. The vessel can now be removed 1836 from the original incision.

Thus, in accordance with the present invention, only one incision is required to harvest and ligate vessel in accordance with the present invention. The use of dissection cradle 312 allows the suture loop 328 of suture 320 to be advanced safely to the surgical site without being caught on the main trunk of the vessel or side branches thereof. The tension mount 308 accurately and reliably positions the vessel for transection and the suture 320 for cutting and provides the tension required to tighten the suture loop 328 of suture 320 onto a forward shoulder of the curved channel 304 for safe advancement and tensioning as required to provide hemostasic transection and harvesting of a target vessel.

The invention claimed is:

1. A surgical apparatus, comprising:
a cannula having a proximal end, a distal end, and a lumen extending between the proximal and distal ends;
a surgical tool moveably coupled to the cannula, wherein the surgical tool includes a cutting instrument; and
a retractor slidably coupled to the cannula, the retractor having a support housed within the lumen and a rigid cradle coupled to a distal end of the support;
wherein the support is configured for displacing the rigid cradle laterally away from a central axis of the cannula in response to a translation of the retractor relative to the cannula; and
wherein the cradle is configured to engage a target vessel, and the cutting instrument is configured to sever a branch vessel of the target vessel while the cradle is engaged with the target vessel;
wherein the support includes two arms that are spaced apart from each other.

2. The surgical apparatus of claim 1, wherein an orientation of the cradle as a whole relative to the cannula is variable as a function of an amount of displacement of the retainer relative to the cannula.

3. The surgical apparatus of claim 2, wherein the orientation of the cradle relative to the cannula is variable from 0° to an angle having a value that is less than 180°.

4. The surgical apparatus of claim 1, wherein a distance between the cradle and the central axis of the cannula is variable as a function of an amount of displacement of the retainer relative to the cannula.

5. The surgical apparatus of claim 4, wherein an orientation of the cradle relative to the cannula is variable as the function of the amount of displacement of the retainer relative to the cannula.

6. The surgical apparatus of claim 1, wherein the support includes a portion that is parallel to the central axis of the cannula.

7. The surgical apparatus of claim 1, wherein the support is bendable.

8. The surgical apparatus of claim 1, wherein the rigid cradle has a shape that remains constant regardless of an amount of relative translation between the retractor and the cannula.

9. The surgical apparatus of claim 1, wherein the cradle has a U-shape.

10. The surgical apparatus of claim 1, wherein the surgical tool is slidably coupled to the cannula.

11. The surgical apparatus of claim 1, wherein the retractor is configured to displace a vessel away from the surgical tool in response to a movement of the retractor relative to the cannula.

12. The surgical apparatus of claim 1, wherein the cradle is aligned with a space that is between the two arms.

13. The surgical apparatus of claim 1, further comprising an endoscope lumen in the cannula.

14. The surgical apparatus of claim 1, wherein the cradle includes a recess for accommodating a vessel.

15. A surgical apparatus, comprising:
a cannula having a proximal end, a distal end, and a lumen extending between the proximal and distal ends;
a surgical tool moveably coupled to the cannula, wherein the surgical tool includes a cutting instrument; and
a retractor slidably coupled to the cannula, the retractor having a cradle, wherein the cradle is capable of being placed at a position that is distal to the distal end of the cannula, the cradle having a shape at the position;
wherein the cradle with the shape is moveable away from a central axis of the cannula in response to a translation of the retractor relative to the cannula; and
wherein the cradle is configured to engage a target vessel, and the cutting instrument is configured to sever a branch vessel of the target vessel while the cradle is engaged with the target vessel;
wherein the retractor further includes two arms that are spaced apart from each other.

16. The surgical apparatus of claim 15, wherein an orientation of the cradle as a whole relative to the cannula is variable as a function of an amount of displacement of the retainer relative to the cannula.

17. The surgical apparatus of claim 16, wherein the orientation of the cradle relative to the cannula is variable from 0° to an angle having a value that is less than 180°.

18. The surgical apparatus of claim 15, wherein a distance between the cradle and the central axis of the cannula is variable as a function of an amount of displacement of the retainer relative to the cannula.

19. The surgical apparatus of claim 18, wherein an orientation of the cradle relative to the cannula is variable as the function of the amount of displacement of the retainer relative to the cannula.

20. The surgical apparatus of claim 15, wherein the retractor further includes a portion that is parallel to the central axis of the cannula.

21. The surgical apparatus of claim 15, wherein the retractor further includes a support that is bendable.

22. The surgical apparatus of claim 15, wherein the cradle is rigid and has a shape that remains constant regardless of an amount of relative translation between the retractor and the cannula.

23. The surgical apparatus of claim 15, wherein the cradle has a U-shape.

24. The surgical apparatus of claim 15, wherein the surgical tool is slidably coupled to the cannula.

25. The surgical apparatus of claim 15, wherein the retractor is configured to displace a vessel away from the surgical tool in response to a movement of the retractor relative to the cannula.

26. The surgical apparatus of claim 15, wherein the cradle is aligned with a space that is between the two arms.

27. The surgical apparatus of claim 15, further comprising an endoscope lumen in the cannula.

28. The surgical apparatus of claim 15, wherein the cradle includes a recess for accommodating a vessel.

* * * * *